United States Patent [19]

Webb

[11] 4,252,803
[45] Feb. 24, 1981

[54] INDOLE COMPOUNDS AND USE THEREOF

[75] Inventor: Colin F. Webb, Royston, England

[73] Assignee: Glaxo Group Limited, London, England

[21] Appl. No.: 83,343

[22] Filed: Oct. 10, 1979

[30] Foreign Application Priority Data

Oct. 12, 1978 [GB] United Kingdom ............... 40279/78

[51] Int. Cl.³ ................. C07D 209/20; C07D 413/06; A61K 31/40; A61K 31/535
[52] U.S. Cl. ........................... 424/248.5; 424/248.54; 424/250; 424/274; 424/248.56; 542/422; 544/80; 544/143; 544/357; 544/373; 260/326.12 R; 260/326.14 R
[58] Field of Search ................. 544/80, 143, 357, 373; 260/326.12 R, 326.14 R; 424/248.5, 248.54, 250, 274, 248.56; 542/422

[56] References Cited

U.S. PATENT DOCUMENTS 3,182,071 5/1965 Shavel et al. ........................ 260/319

FOREIGN PATENT DOCUMENTS 419016 5/1966 Japan .

OTHER PUBLICATIONS

Stadler et al., European Patent Application, No. 0,000,355 1-24-79.
Shavel et al., JACS, vol. 84 (1962), pp. 881–882.

Primary Examiner—Henry R. Jiles
Assistant Examiner—R. W. Ramsuer
Attorney, Agent, or Firm—Bacon & Thomas

[57] ABSTRACT

Compounds are disclosed of general formula (I):

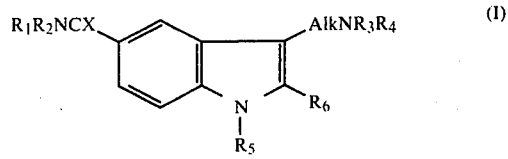

wherein
$R_1$ and $R_2$ each independently represents a hydrogen atom, or an aryl, aralkyl, cycloalkyl, fluoroalkyl or alkyl group, which alkyl group is optionally substituted by an alkenyl group or by a group -$OR_7$ or by

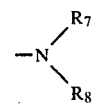

where $R_7$ and $R_8$ each independently represents a hydrogen atom, an alkyl, aryl or aralkyl group; or $R_1$ and $R_2$ together with the nitrogen atom to which they are attached form a saturated monocyclic 5 to 7 membered ring which may contain a further hetero function (viz—O—, —NH or

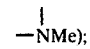

$R_3$ and $R_4$ have the same meanings as $R_1$ and $R_2$ and may together form an aralkylidene group;
$R_5$ represents a hydrogen atom or an alkyl or aralkyl group;
$R_6$ represents a hydrogen atom or an aryl or $C_1$-$C_3$ alkyl group;
Alk represents an $C_1$-$C_4$ alkylene group optionally substituted at one or more of its carbon atoms by one to three $C_1$-$C_3$ alkyl groups; and
X represents an oxygen or sulphur atom,
and its physiologically acceptable salts, hydrates and bioprecursors.

The indoles (I) may be prepared by combinations of reactions to introduce the desired substituents into suitable intermediates either before or after cyclization to form the indole nucleus. The compounds have selective actions on blood vessels and, in particular exhibit antihypertensive properties. They may be formulated in conventional manner as pharmaceutical compositions.

14 Claims, No Drawings

INDOLE COMPOUNDS AND USE THEREOF

This invention relates to certain heterocyclic compounds, to processes for their preparation, to pharmaceutical compositions containing them and to their medical use.

Thus, the present invention provides an indole of the general formula (I):

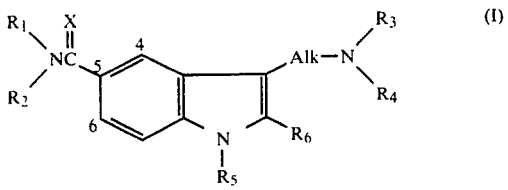

wherein $R_1$ and $R_2$, which may be the same or different, each represents a hydrogen atom, or an aryl, aralkyl, cycloalkyl, fluoroalkyl or alkyl group, which alkyl group may be unsubstituted or substituted by an alkenyl group or by a group $-OR_7$ or by a group

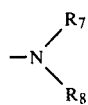

where $R_7$ and $R_8$, which may be the same or different, each represents a hydrogen atom, an alkyl, aryl or aralkyl group; or $R_1$ and $R_2$ together with the nitrogen atom to which they are attached form a saturated monocyclic 5 to 7 membered ring which may contain a further hetero function (viz oxygen or the group

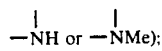

$R_3$ and $R_4$, which may be the same or different, each represents a hydrogen atom, or an aryl, aralkyl, cycloalkyl, fluoroalkyl or alkyl group, which alkyl group may be unsubstituted or substituted by an alkenyl group or by a group $-OR_7$ or by a group

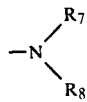

where $R_7$ and $R_8$ are as previously defined;
or $R_3$ and $R_4$ may together form an aralkylidene group; or $R_3$ and $R_4$ together with the nitrogen atom to which they are attached form a saturated monocyclic 5 to 7 membered ring which may contain a further hetero function (viz oxygen or the group

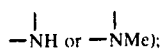

$R_5$ represents a hydrogen atom or an alkyl or aralkyl group;

$R_6$ represents a hydrogen atom or an aryl or $C_1-C_3$ alkyl group;

Alk represents an alkylene group of one to four carbon atoms in chain length, which group may be unsubstituted or substituted at one or more of its carbon atoms by one to three $C_1-C_3$ alkyl groups; and X represents an oxygen or sulphur atom,
and its physiologically acceptable salts, hydrates and bioprecursors.

The compounds according to the invention include all optical isomers thereof and their racemic mixtures.

Referring to the general formula (I), the alkyl group may be a straight chain or branched chain alkyl group preferably containing from 1 to 6 carbon atoms unless otherwise specified. The cycloalkyl group preferably contains 5 to 7 carbon atoms. The fluoroalkyl group is a $C_1-C_3$ alkyl group substituted with not more than three fluorine atoms which may be attached to one or more of the carbon atoms. The term aryl used as such or in the term aralkyl preferably means phenyl which may be substituted by one or more alkyl groups (for example, methyl), halogen atoms (for example, fluorine), hydroxy groups or methoxy groups. The alkyl moiety of the aralkyl group preferably contains 1 to 6 carbon atoms. The alkenyl groups preferably contains 2 to 4 carbon atoms. The aralkylidene group is preferably an arylmethylidene group.

In the general formula (I), $R_1$ and $R_2$ are preferably both hydrogen atoms.

It is preferred that one or both of $R_3$ and $R_4$ are hydrogen or $C_1-C_3$ alkyl groups or $R_3$ is a hydrogen atom and $R_4$ is an aralkyl group. $R_5$ and $R_6$ are preferably both hydrogen atoms.

The group represented by Alk is preferably a $C_2-C_3$ alkylene group which is preferably unsubstituted.

X is preferably oxygen.

In the embodiment wherein $R_1$ and $R_2$ or $R_3$ and $R_4$ together with the nitrogen atom to which they are attached form a saturated monocyclic ring, the monocyclic ring is preferably morpholino.

According to a particular embodiment of the present invention it is preferred that $R_1$ is a hydrogen atom and that $R_2$ is a hydrogen atom, an aralkyl group preferably benzyl, a cycloalkyl group preferably cyclopentyl, an unsubstituted alkyl group preferably methyl or an alkyl group substituted by an alkenyl group or the group $-OR_7$ preferably hydroxymethyl or allyl.

According to another embodiment, it is preferred that $R_3$ is a hydrogen atom or an alkyl group preferably methyl or n-propyl and that $R_4$ is a hydrogen atom, a fluoroalkyl group preferably trifluoroethyl, an unsubstituted alkyl group preferably methyl or n-propyl or an aralkyl group preferably benzyl or a group $CH_3CH(CH_2)pPh$ where p is 1, 2 or 3 and the phenyl group (Ph) may be substituted by a p-chloro group. Alternatively, it is preferred that $R_3$ and $R_4$ together form an aralkylidene group preferably benzylidene or together with the nitrogen atom to which they are attached form a saturated monocyclic 5 to 7 membered ring containing a further hetero function preferably morpholino or piperazino.

According to another embodiment, it is preferred that $R_5$ is a hydrogen atom, an alkyl group preferably methyl or a benzyl group.

According to a further embodiment, it is preferred that $R_6$ is a hydrogen atom or an alkyl group preferably methyl.

According to a further aspect of the invention it is preferred that Alk is an alkylene group containing 2 or 3 carbon atoms and is preferably unsubstituted.

According to a particularly preferred embodiment of the invention $R_1$ is a hydrogen atom and $R_2$ is a hydrogen atom or a methyl or hydroxymethyl group.

According to another particularly preferred embodiment $R_3$ is a hydrogen atom or a methyl group and $R_4$ is a hydrogen atom or a methyl, trifluoroethyl or benzyl group or a group $CH_3CH(CH_2)_2Ph$ (where Ph represents an unsubstituted phenyl group). Alternatively it is particularly preferred that $R_3$ and $R_4$ together with the nitrogen atom to which they are attached represent a benzylidene or morpholino group.

It is particularly preferred that $R_5$ represents a hydrogen atom or a methyl group.

According to a further particularly preferred embodiment $R_6$ represents a hydrogen atom.

It is further particularly preferred that Alk represents an unsubstituted alkylene chain containing 2 or 3 carbon atoms.

In the particularly preferred embodiment of the invention X is preferably an oxygen atom.

Preferred compounds according to the invention are:-
3-(2-aminoethyl)-1$\underline{H}$-indole-5-carboxamide;
3-[2-[(1-methyl-3-phenylpropyl)amino]ethyl]-1$\underline{H}$-indole-5-carboxamide;
3-[2-(dimethylamino)ethyl]-1$\underline{H}$-indole-5-carboxamide;
3-[2-(methylamino)ethyl]-1$H$-indole-5-carboxamide;
3-[2-(4-morpholinyl)ethyl]-1$\underline{H}$-indole-5-carboxamide;
3-(2-aminoethyl)-1$\underline{H}$-indole-5-carbothioamide;
3-(3-aminopropyl)-1$\underline{H}$-indole-5-carboxamide;
3-[2-(2,2,2-trifluoroethyl)aminoethyl]-1$\underline{H}$-indole-5-carboxamide;
and their physiologically acceptable salts.

Suitable physiologically acceptable salts of the indoles of general formula (I) are acid addition salts formed with organic or inorganic acids, for example, hydrochlorides, hydrobromides, sulphates, fumarates, maleates and creatinine sulphate adducts.

The compounds of the invention have been shown to have selective actions on blood vessels such that they may be useful in the treatment of cardiovascular disorders such as hypertension, Raynaud's disease and migraine.

The antihypertensive properties of the compounds of the invention have been demonstrated by their ability to lower blood pressure in tests performed on hooded rats made hypertensive by DOCA implantation and by replacement of their drinking water with isotonic saline for 8 weeks. The compounds of the invention when administered intraperitoneally were found to lower blood pressure in conscious hypertensive rats in some instances for a period of several hours.

The potential use of certain compounds of the invention in the treatment of migraine is indicated by the fact that they have a selective contractile action on the dog isolated ear artery. Methysergide, which is known to be useful in the treatment of migraine, shows this same action (W. Feniuk, P. P. A. Humphrey and G. P. Levy, Br. J. Pharmacology 1977, 61, 466).

Accordingly, the invention also provides a pharmaceutical composition which comprises at least one compound selected from indole derivatives of the general formula (I), their physiologically acceptable salts, hydrates and bioprecursors adapted for use in human or veterinary medicine, and formulated for administration by any convenient route.

Such compositions may be formulated in conventional manner using one or more physiologically acceptable carriers or excipients. Such compositions may also contain other active ingredients, e.g. conventional β-blocking agents, such as propranolol.

Thus the compounds according to the invention may be formulated for oral, buccal, parenteral or rectal administration. Oral administration is preferred.

For oral administration, the pharmaceutical compositions may take the form of, for example, tablets, capsules, solutions, syrups or suspensions prepared by conventional means with physiologically acceptable excipients. For buccal administration the composition may take the form of tablets or lozenges formulated in conventional manner.

The compounds of the invention may be formulated for parenteral administration by bolus injection or continuous infusion. Formulations for injection may be presented in unit dosage form in ampoules, or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

The compounds of the invention may also be formulated in rectal compositions such as suppositories or retention enemas, e.g., containing conventional suppository bases such as cocoa butter or other glyceride.

A proposed dose of the compounds of the invention for oral administration to man, in order effectively to lower the blood pressure, is 5 mg–500 mg total daily dose which may be administered, for example, in up to 4 or 5 doses per day.

The compounds of general formula (I) may generally be prepared by an appropriate combination of reactions by which the desired substitutents are introduced into suitable intermediates, either before or after cyclisation to form the indole nucleus.

The following are given as examples of processes for the preparation of the compounds of the invention. It may be necessary or desirable to perform a sequence of two or more reaction steps in order to obtain the desired substitution. Where necessary, other substituent groups already present on the indole nucleus may be protected in conventional manner, during a reaction to introduce or modify another substituent.

According to one process, for the preparation of a compound of general formula (I) in which X is an oxygen atom, an activated carboxylic acid derivative of general formula (II):

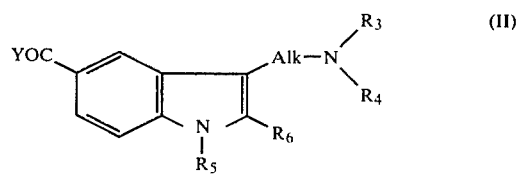

where Alk, $R_3$, $R_4$, $R_5$ and $R_6$ are as previously defined and Y is a leaving group, is reacted with a reagent of general formula $R_1R_2NH$ in which $R_1$ and $R_2$ are as previously defined.

Suitable activated carboxylic acid derivatives represented by the general formula (II) include acyl hlaides (e.g. acid chlorides), esters (e.g. methyl, p-nitrophenyl or 1-methylpyridinium esters), acid anhydrides (in particular mixed acid anhydrides), and the products formed by reaction of the appropriate carboxylic acid corresponding to general formula (II), in which Y is a hydroxyl group, with a coupling agent such as carbonyl diimidazole or dicyclohexylcarbodiimide. These activated carboxylic acid derivatives may be formed from the corresponding acid by well known procedures. For example, acid chlorides may be prepared by reaction with phosphorus pentachloride, thionyl chloride or oxalyl chloride; esters (e.g. alkyl esters) may be prepared by reaction with an alcohol (e.g. methanol) in the presence of an acid catalyst such as a mineral acid (e.g. hydrochloric acid), and 1-methypyridinium esters (II,

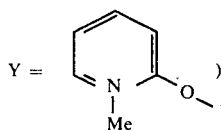

may conveniently be prepared by reaction with a 2-halo-1-methylpyridinium iodide in the presence of an amine (e.g. triethylamine); and mixed acid anhydrides may be prepared by reaction with an appropriate acid anhydride (e.g. trifluoroacetic anhydride), an acid chloride (e.g. acetyl chloride or 1-[(diphenylamino)carbonyl]pyridinium chloride) or an alkyl or aralkyl haloformate (e.g. ethyl or benzyl chloroformate).

The conditions under which the activated carboxylic acid derivative of general formula (II) is formed and subsequently reacted with the reagent of formula $R_1R_2NH$ will depend upon the nature of the activated derivative and the reagent $R_1R_2NH$. Thus the reaction between an ester of formula (II) and the reagent of formula $R_1R_2NH$ may conveniently be carried out in a solvent such as water or an alkanol (e.g. methanol), or the reagent may itself also act as solvent. A temperature appropriate to the reaction is used, which may be up to and including the reflux temperature of the mixture.

Where it is desired to prepare a compound of general formula (I) in which one or both of $R_3$ and $R_4$ represent hydrogen it is frequently necessary, in the above reactions, to protect the group $NR_3R_4$, for example as a phthalimide (in the case of a primary amine), an N-benzyl derivative, and N-benzyl-oxycarbonyl derivative or an N-trichloroethyl urethane. Such protection is essential when the activated derivative represented by formula (II) is an acid chloride or acid anhydride. Subsequent cleavage of the protecting group is achieved by conventional procedures. Thus a phthalimido group may be cleaved by treatment with hydrazine hydrate or a primary amine for example methylamine, and an N-benzyl or N-benzyloxycarbonyl derivative may be cleaved by hydrogeneolysis in the presence of a catalyst, for example palladium. An N-benzyloxycarbonyl group may also be cleaved by treatment with hydrogen bromide in acetic acid.

According to another process for preparing a compound of general formula (I) in which $R_1$ and $R_2$ are both hydrogen, the $-CXNH_2$ group is introduced by reaction of a nitrile of general formula (III):

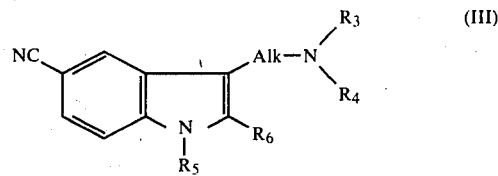

wherein Alk, $R_3$, $R_4$, $R_5$ and $R_6$ are as previously defined, with a suitable oxygen- or sulphur-containing compound.

According to one embodiment of this process for preparing a compound of general formula (I) wherein X is oxygen, a nitrile of general formula (III) may be hydrolysed with acid or alkali under controlled conditions to yield the desired 5-caboxamide. Thus, for example, the nitrile of formula (III) may be heated under reflux in a mixture of concentrated sulphruic acid, acetic acid and water (1:1:1) or with acetic acid containing boron trifluoride. Another possibility is to treat the nitrile of formula (III) with the hydroxide form of an anion exchange resin (e.g. Amberlite IRA 400) in a solvent such as ethanol or water at reflux or with a base, for example potassium hydroxide or potassium tertiary butoxide, in a solvent, for example tertiary butanol, at reflux.

According to another embodiment of this process for preparing a compound of general formula (I) wherein X is sulphur, a nitrile of general formula (III) may be treated with, for example, hydrogen sulphide in a solvent (e.g. dimethylformamide or pyridine).

In this embodiment of the process, when $R_3$ and/or $R_4$ is a hydrogen atom, the $-NR_3R_4$ group should preferably be protected, for example as the N-phthalimide, during the treatment with hydrogen sulphide with subsequent removal of the protecting group to yield the desired 5-thioamide.

A compound of general formula (I) according to the invention may also be prepared by conversion of another compound of the general formula (I).

For example, a compound of general formula (I), wherein $R_5$ and/or $R_3$ and $R_4$ are hydrogen atoms, may be converted into another compound of general formula (I), wherein $R_5$ and/or at least one of $R_3$ and $R_4$ is other than hydrogen, by a variety of alkylation procedures. Thus, it is possible, according to the present invention, selectively to introduce by alkylation either the $R_5$ group or one or both of the groups $R_3$ and $R_4$, it being understood that when preparing a compound of general formula (I) in which $R_5$ is a hydrogen atom it may be necessary to replace this hydrogen atom by a protecting group which may subsequently be removed. Similarly, when preparing a compound of general formula (I) wherein either or both of $R_3$ and $R_4$ are hydrogen atoms then a protecting group may be necessary.

Thus, a particularly useful procedure for the preparation of a compound of general formula (I) in which X is oxygen and one of $R_3$ and $R_4$ is hydrogen is reductive alkylation of the corresponding compound of formula (I) in which $R_3$ and $R_4$ are both hydrogen with an appropriate ketone or aldehyde (e.g. acetone or benzaldehyde) in the presence of a suitable catalyst (e.g. 10% palladium on charcoal). Alternatively the aldehyde or ketone may be condensed with the primary amine and the intermediate thus formed may subsequently be reduced using, for example, sodium borohydride or sodium cyanoborohydride or hydrogen in the presence of a metal catalyst (e.g. palladium).

According to another possibility, alkylation (e.g. methylation) may be effected by treating a primary amine of general formula (I) (i.e. in which R₃ and R₄ are both hydrogen) with formaldehyde and formic acid (the Eschweiler-Clarke procedure). This method is particularly suitable for the preparation of N,N-disubstituted products of general formula (I), in which $R_3$ and $R_4$ are both the same and other than hydrogen. Alternatively a secondary amine (i.e. in which $R_3$ is hydrogen and $R_4$ is other than hydrogen) may be used, to give a tertiary amine of general formula (I) in which $R_3$ and $R_4$ may be the same or different.

A further possibility is to react a primary amine of formula (I) (i.e. in which $R_3$ and $R_4$ are both hydrogen) with an appropriate halide (e.g. iodoethanol) in a solvent such as acetone and preferably under reflux, followed by treatment with a base (e.g. sodium hydroxide) to produce an N-substituted amine of general formula (I) in which at least one of $R_3$ and $R_4$ is other than hydrogen.

In another process, treatment of a primary amine of general formula (I) (i.e. where both $R_3$ and $R_4$ are hydrogen) with an aromatic aldehyde (e.g. benzaldehyde) followed by reaction with an alkyl halide (e.g. methyl iodide) in a solvent (e.g. aqueous 95% ethanol) gives, after heating under reflux, an N-substituted amine of general formula (I) where one of $R_3$ and $R_4$ is other than hydrogen.

Compounds of general formula (I) in which the moiety $NR_3R_4$ forms a heterocyclic ring may be prepared by treating the corresponding primary amine of general formula (I) (i.e. in which $R_3=R_4=H$) with, for example, an α,ω-dihalocompound such as an α,ω-dihaloalkane (e.g. 1,5-dibromopentane) or an α,ω-dihalodialkyl ether (e.g. 2,2'-dichlorodiethyl ether).

The introduction of an alkyl group represented by $R_5$ may be carried out by alkylation with an appropriate alkyl or aralkyl halide or dialkyl sulphate preferably in the presence of a base such as sodium hydride in a solvent such as dimethylformamide.

According to another process the group Alk $NR_3R_4$ may be interconverted to another group of formula Alk $NR_3R_4$ by reduction. For example, a compound of general formula (I) wherein $R_3$ is a benzyl group may be reduced in the presence of a suitable catalyst such as palladium on charcoal in a solvent such as ethanol to yield a compound of general formula (I) wherein $R_3$ is a hydrogen atom.

The aminoalkyl substituent ($-Alk-NR_3R_4$) may be introduced into the indole nucleus by a variety of conventional techniques which may, for example, involve modification of a substituent in the 3-position, direct introduction of the aminoalkyl substituent into the 3-position or introduction of the aminoalkyl substituent prior to cyclisation to form the indole nucleus. In general the processes involved are based on methods referred to in 'A Chemistry of Heterocyclic Compounds—Indoles Part II', chapter VI (3), edited by William J. Houlihan (1972), Wiley Interscience New York.

A compound of general formula (I) in which X is an oxygen atom and Alk is a 2-carbon chain may be prepared by reduction of a compound or general formula (IV):

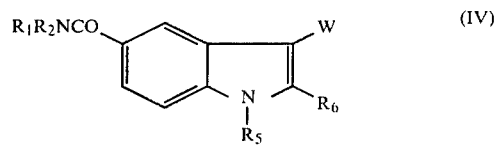

where
$R_1$, $R_2$, $R_5$ and $R_6$ are as previously defined and
W represents the group $-CHR_9CN$, $CH_2CHR_9NO_2$ $-CH=CR_9NO_2$ or $-COCHR_9Z$ (where $R_9$ is a hydrogen atom or a $C_1-C_3$ alkyl group and Z is an azido group $N_3$ or an amino group $NR_3R_4$)
with the proviso that, except where W represents the group $-COCHR_9Z$ and Z is an amino group $NR_3R_4$, $R_3$ and $R_4$ in the resulting compound of general formula (I) are both hydrogen atoms.

According to a modification of this process the 5-substituent may be a group convertible to a $R_1R_2NCO-$ group.

Thus, for example, according to a first embodiment, a compound of general formula (1) in which $R_3$ and $R_4$ are both hydrogen and Alk is a 2-carbon chain which may be unsubstituted or substituted by a $C_{1-3}$ alkyl group on either carbon atom, may be prepared by catalytic reduction of a corresponding nitrile of general formula (V) or by reduction of a nitrocompound of general formula (VI) with Raney nickel and hydrogen

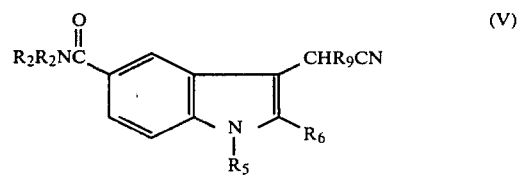

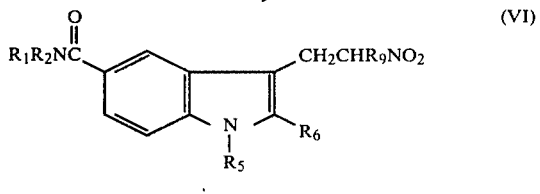

in which
$R_1$, $R_2$, $R_5$, $R_6$ and $R_9$ are as defined previously.

According to a second embodiment, an aminoethyl derivative of general formula (I), in which $R_3$ and $R_4$ are both hydrogen and the carbon atom adjacent to the amino group may be unsubstituted or substituted by a $C_{1-3}$ alkyl group, may be prepared by reduction (e.g. using hydrogen in the presence of a catalyst such as palladium) of a corresponding 3-nitrovinylindole of general formula (VII):

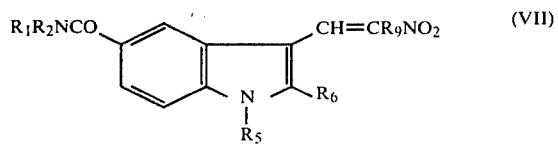

in which $R_1$, $R_2$, $R_5$, $R_6$ and $R_9$ are as defined previously.

According to a third embodiment of the reduction process, a compound of general formula (I) in which Alk is a 2-carbon chain which may be unsubstituted or substituted with a $C_{1-3}$ alkyl group at the carbon atom adjacent to the amino group-$NR_3R_4$, may be prepared by reduction of the azidoketone or aminoacylindole of general formula (VIII):

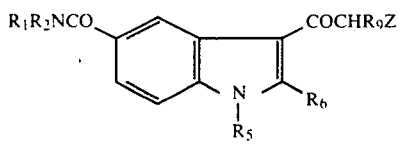
(VIII)

in which $R_1$, $R_2$, $R_5$, $R_6$, $R_9$ and $Z$ are as defined previously.

This reduction may, for example, be effected catalytically or by the use of sodium borohydride in propanol. When an azidoketone (VIII, $Z=N_3$) is reduced the product is a 2-aminoethyl derivative in which $R_3$ and $R_4$ are both hydrogen; reduction of an aminoacylindole (VIII, $Z=NR_3R_4$) affords a 2-aminoethyl derivative in which one or both of $R_3$ and $R_4$ may be other than hydrogen.

According to a modification of this process where $Z$ is $NR_3R_4$ then the 5-substituent may be a group convertible into a $R_1R_2NCO$—group, for example a cyano group, wherein the reduction reaction is followed by conversion of the 5-substituent into the desired $R_1R_2NCO$—group for example by hydrolysis with acid or alkali.

The starting materials for the first embodiment of the reduction process described, having the general formula (V) or (VI), may be prepared by quaternisation of the appropriate compound of formula (IX):

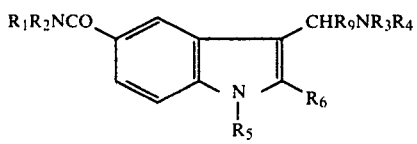
(IX)

wherein $R_1$, $R_2$, $R_3$, $R_4$, $R_5$, $R_6$ and $R_9$ are as previously defined
with an alkyl halide of general formula $R_{10}Hal$ (where $R_{10}$ represents an alkyl group), and subsequent reaction of the quaternary salt of general formula (X):

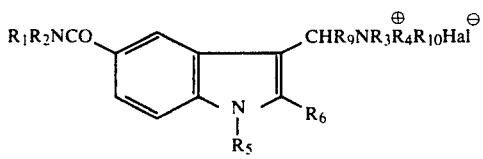
(X)

with either an alkali metal cyanide or an alkli metal salt of a nitroalkane to give the corresponding nitrile (V) or nitro compound (VI) respectively.

Alternatively the nitrocompound (VI) may be prepared by reaction of the Mannich base (IX) with an alkali metal salt of a nitroalkane.

The 3-aminomethyl derivative of general formula (IX) may be prepared by subjecting an indole of formula (XI):

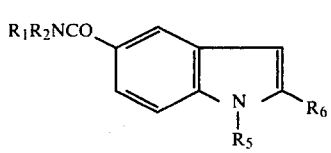
(XI)

wherein
$R_1$, $R_2$, $R_5$ and $R_6$ are as previously defined
to a Mannich reaction using a primary or secondary amine of formula $R_3R_4NH$ and an aldehyde of formula $R_9CHO$ (where $R_9$ is a hydrogen atom or a $C_1$-$C_3$ alkyl group) e.g. formaldehyde.

The nitrovinylindole used as starting material for the second embodiment of the reduction process, having the general formula (VII) may be obtained by the action of a nitroalkane or general formula $R_9CHNO_2$ on a corresponding 3-formylindole of general formula (XII):

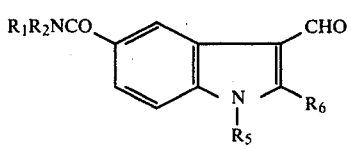
(XII)

in which $R_1$, $R_2$, $R_5$ and $R_6$ are as previously defined.

The compound of general formula (XII) may be prepared by carrying out a Vilsmeier reaction (e.g. using phosphorus oxychloride and dimethylformamide) on an indole of formula (XIII):

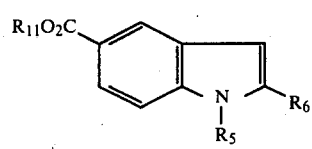
(XIII)

wherein
$R_{11}$ is a lower alkyl group with subsequent conversion of the ester into the amidic group —$CONR_1R_2$, thereby giving the 3-formylindole of formula (XII) as just defined.

The azidoketone or aminoacylindole starting material for the third embodiment of the reduction process, having the general formula (VIII), may be obtained from a corresponding haloacylindole of general formula (VIII) in which $Z$ represents a halogen atom, by treatment with sodium azide or an amine of formula $R_3R_4NH$ respectively.

The haloacylindole (VIII, $Z=Hal$) may be prepared by halogenation (e.g. bromination using N-bromosuccinimide) of the corresponding acylindole (VIII, $Z=H$), which may itself be obtained from an indole of general formula (XI) by treatment with, for example, an acyl halide of formula $R_9CH_2COHal$.

Compounds of formula (I) in which Alk represents an alkylene chain containing one, two, three or four carbon atoms may, in general, be prepared by application of the Fischer-indole synthesis, whereby a phenylhydrazone of general formula (XIV):

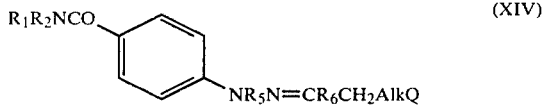

in which Q is the group $NR_3R_4$ or a halogen atom (e.g. chlorine), is cyclised by a variety of methods.

When Q is the group $NR_3R_4$ the phenylhydrazone of formula (XIV) is cyclised by heating in the presence of an appropriate catalyst such as zinc chloride.

When Q is a halogen atom cyclisation is effected by heating in an aqueous alkanol (e.g. methanol) to give a product of formula (I) in which $R_3$ and $R_4$ are both hydrogen.

The phenylhydrazone of formula (XIV) in which Q is $NR_3R_4$ may be prepared by reacting a phenylhydrazine of formula (XV):

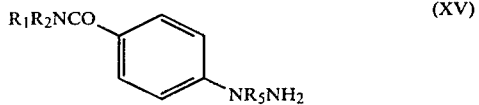

with an appropriate aldehyde or ketone of formula (XVI):

(or a derivative thereof such as an acetal or ketal) in a suitable solvent (e.g. aqueous acetic acid).

The phenylhydrazone of formula (XIV) in which Q is a halogen atom may be prepared by condensing a substituted phenylhydrazine of formula (XV) with a haloketone $R_6COCH_2AlkHal$ (in which Hal is e.g. chlorine) in a solvent (e.g. ethanol).

According to a modification of the above process the 5-substituent may be a group convertible to a $R_1R_2NCO$—group, e.g. a cyano group, wherein the cyclisation step is followed by conversion of the 5-substituent into the desired $R_1R_2NCO$—group.

In the above synthesis, when Q is the group $NR_3R_4$ and $R_3$ and/or $R_4$ are hydrogen, the amino group $NR_3R_4$ is preferably protected (e.g. as a phthalimide or N-benzyl derivative) as described previously.

A further general method for preparing compounds of general formula (I) involves displacement of the halogen function from a 3-haloalkylindole of formula (XVII):

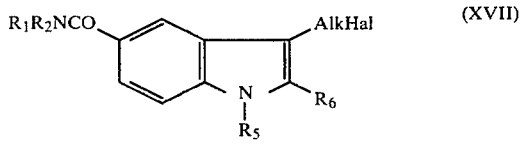

in which $R_1$, $R_2$, $R_5$, $R_6$ and Alk are as defined for formula (I) and the halogen function, Hal, is, for example, chlorine, by reaction with ammonia or an amine of formula $R_3R_4NH$.

The haloalkylindole starting material of general formula (XVII) may be prepared by condensing a substituted phenylhydrazine of formula (XV) with a haloketone $R_6COCH_2AlkHal$ (in which Hal is e.g. chlorine) in a solvent (e.g. ethanol), with heating and in the presence of an acid (e.g. hydrochloric acid).

Where it is desired to isolate a compound of the invention as a salt this may be achieved by treating the free base of general formula (I) with an equivalent amount of an appropriate acid, or with creatinine sulphate in a suitable solvent (e.g. aqueous acetone).

The carboxylic acid derivatives represented by general formula (II) in which the group Y may for example be an alkoxy group, the corresponding carboxylic acids, and the nitriles of formula (III) may in general be prepared by suitable application of one or more of the above described processes for introducing the substituent $—AlkNR_3R_4$ either before or after cyclisation to form the indole nucleus.

Thus, for instance, a nitrile of formula (III) may conveniently be prepared by application of the Fischer-indole synthesis described above by heating a hydrazone of general formula (XVIII):

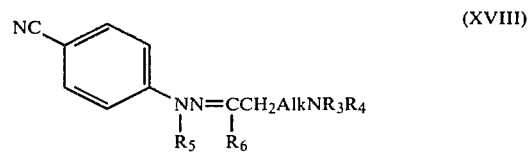

with a catalyst (e.g. polyphosphoric ester) in a solvent (e.g. chlorobenzene).

Hydrazones of formula (XVIII) are prepared from the corresponding hydrazines (XIX):

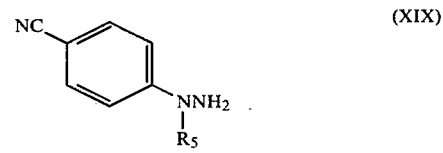

and an aldehyde or ketone of formula (XVI) as previously defined or a derivative thereof such as an acetal or ketal according to the general procedure previously described.

In another process affording a nitrile of formula (III), a haloindole of general formula (XX) is treated with cuprous cyanide in a solvent such as N-methylpyrrolidine at an elevated temperature (e.g. 200° C.).

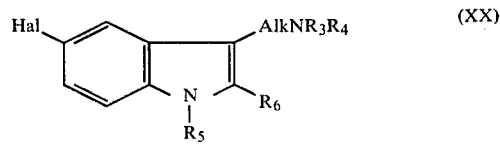

In the above formula (XX), $AlkNR_3R_4$, $R_5$ and $R_6$ are as defined for general formula (I) and Hal represents a halogen atom (e.g. bromine). When preparing nitriles of formula (III) in which $R_3$ and/or $R_4$ represents hydrogen, it is necessary to protect the amino group $NR_3R_4$ (e.g. as a phthalimide or N-benzyl derivative) as described previously.

The haloindole (XX) may be prepared from a halo-substituted phenylhydrazine of general formula (XXI):

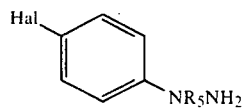

by application of the Fischer indole synthesis as described previously.

If desired a nitrile of formula (III) may be hydrolysed to a carboxylic acid corresponding to formula (II) (Y=OH) by prolonged reflux in either acid or alkali, or converted into an ester of formula (II) (Y=alkoxy) by treatment with an appropriate alkanol (e.g. methanol) in the presence of an acid (e.g. gaseous hydrogen chloride).

In addition a carboxylic acid corresponding to general formula (II) (Y=OH) in which $R_3$, $R_4$, $R_5$ and $R_6$ are hydrogen, and Alk represents a 2-carbon chain, may conveniently be prepared by application of the Abramovitch synthesis, in which a substituted benzenediazonium salt is coupled with a 3-carboxy-2-piperidone to give a hydrazone of formula (XXII):

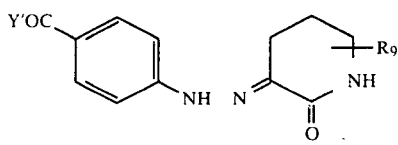

wherein $R_9$ is as previously defined and Y' may be, for example, a hydroxy or alkoxy group, which is then cyclised to a 1,2,3,4-tetrahydro-1-oxo-$\beta$-carboline of general formula (XXIII):

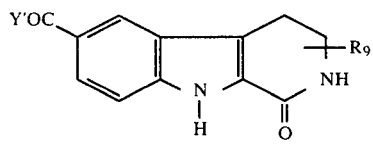

Hydrolysis of the oxocarboline (XXIII) followed by decarboxylation of the resulting indole-2-carboxylic acid gives the desired 3-aminoethylindole derivative.

The invention is illustrated by the following Examples.

EXAMPLES OF PHARMACEUTICAL PREPARATIONS

Tablets

These may be prepared by direct compression or by wet granulation. The direct compression method is preferred but may not be suitable in all cases as it is dependent upon the dose level and physical characteristics of the active ingredient.

| A. Direct compression | mg/tablet |
|---|---|
| Active ingredient | 10.0 |
| Microcrystalline Cellulose B.P.C. | 89.5 |
| Magnesium Stearate | 0.5 |
| Compression Weight | 100.0 |

The active ingredient is sieved through a 250 μm sieve, blended with the excipients and compressed using 6.0 mm punches. Tablets of other strengths may be prepared by altering the compression weight and using punches to suit.

| B. Wet Granulation | mg/tablet |
|---|---|
| Active ingredient | 10.0 |
| Lactose B.P. | 74.5 |
| Starch B.P. | 10.0 |
| Pregelatinised Maize Starch B.P. | 5.0 |
| Magnesium Stearate B.P. | 0.5 |
| Compression Weight | 100.0 |

The active ingredient is sieved through a 250 μm sieve and blended with the lactose, starch and pregelatinised starch. The mixed powders are moistened with purified water, granules are made, dried, screened and blended with the magensium stearate. The lubricated granules are compressed into tablets as described for the direct compression formula.

The tablets may be film coated with suitable film forming materials, e.g. methyl cellulose or hydroxypropyl methyl cellulose using standard techniques. Alternatively the tablets may be sugar coated.

| Capsules | mg/capsule |
|---|---|
| Active ingredient | 10.0 |
| *STA-RX 1500 | 89.5 |
| Magnesium Stearate B.P. | 0.5 |
| Fill Weight | 100.0 |

*A form of directly compressible starch supplied by Colorcon Ltd., Orpington, Kent, England.

The active ingredient is sieved through a 250 μm sieve and then blended with the other ingredients. The mix is filled into No. 2 hard gelatin capsules using a suitable filling machine. Other doses may be prepared by altering the fill weight and if necessary changing the capsule size to suit.

| Sustained Release Tablets | mg/tablet |
|---|---|
| Active ingredient | 50.0 |
| *Cutina H.R. | 20.0 |
| Lactose B.P. | 128.0 |
| Magnesium Stearate B.P. | 2.0 |
| Compression Weight | 200.0 |

*Cutina HR is a grade of microfine hydrogenated castor oil supplied by Sipon Products Ltd., London.

The active ingredient is sieved through a 250 μm sieve and blended with the Cutina HR and lactose. The mixed powders are moistened with Industrial Methylated Spirits 74 O.P., granules are made, dried, screened and blended with the magnesium stearate. The lubricated granules are compressed using 8.5 mm punches to product tablets with a hardness of not less than 10 Kp (Schleuniger tester).

| Syrup | mg/5ml dose |
|---|---|
| Active ingredient | 10 |
| Sucrose B.P. | 2750.00 |
| Glycerine B.P. | 500.00 |
| Buffer | |
| Flavour | |
| Colour | As required |
| Preservative | |
| Distilled water | 5.00ml |

The active ingredient, buffer, flavour, colour and preservative are dissolved in some of the water, and the glycerine is added. The remainder of the water is heated to 80° C. and the sucrose is dissolved in this and cooled. The two solutions are combined, adjusted to volume and mixed. The syrup produced is clarified by filtration.

| Injection for Intravenous Administration. | % w/v |
|---|---|
| Active ingredient | 0.20 |
| Water for injections B.P. to | 100.00 |

Sodium chloride may be added to adjust the tonicity of the solution and the pH may be adjusted to that of maximum stability using either dilute acid or alkali.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

PREPARATION 1

3-[2-[[(Phenylmethoxy)carbonyl]amino]ethyl]-1H-indole-5carboxylic acid

A vigorously stirred solution of 3-(2-amino-ethyl)-1H-indole-5-carboxylic acid (50 g) in aqueous sodium hydroxide (1 M, 450 ml) was cooled in an icebath and benzyl chloroformate (60 ml) and aqueous sodium hydroxide (1 M, 430 ml) were added simultaneously dropwise over a period of 1 hour so as to maintain the pH > 10. The reaction mixture was stirred at ca 5° C. for 1.25 hour then a further portion of aqueous sodium hydroxide (1 M, 130 ml) was added. After a further 2 hour. the reaction mixture was extracted with ether (2×500 1 ml) and the aqueous layer treated with sodium chloride (200 g), acidified to pH 1 with concentrated hydrochloric acid (80 ml) and extracted with ethyl acetate (3×500 ml). The combined extracts were washed with aqueous sodium chloride (10%, 2×500 ml) dried (MgSO$_4$) and evaporated to dryness to give the title compound as a white solid (61.8 g) mp 186.5°–188°.

Analysis Found: C, 67.4; H, 5.4; N, 8.1%; C$_{19}$H$_{18}$N$_2$O$_4$ requires: C, 67.5; H, 5.3; N, 8.3%.

PREPARATION 2

[2-[5-(Aminocarbonyl)-1H-indol-3-yl]ethyl]carbamic acid, phenylmethyl ester, compound with 2-propanol (1:1)

A solution of 3-[2-[[(phenylmethoxy)carbonyl]amino]ethyl]-1H-indole-5-carboxylic acid (1.7 g) and triethylamine (2.0 ml) in acetonitrile (100 ml) was added to a stirred suspension of 2-iodo-1-methylpyridinium iodide (3.5 g) in acetonitrile (100 ml) and the mixture was warmed to 50° for 90 mins. Ammonia was bubbled through the reaction mixture for 10 mins. After 30 mins, the resulting yellow solution was evaporated to dryness and partitioned between ethyl acetate (200 ml) and sodium hydroxide solution (1 N, 100 ml). The organic phase was washed with dilute sulphuric acid (2 N, 3×100 ml), water (100 ml), dried (Na$_2$SO$_4$) and evaporated to dryness to give a colourless foam (1.7 g) which was crystallised from 2-propanol to give the title amide as a white crystalline solid (1.2 g) m.p.134.5°–135.5° C.

A sample for analysis was recrystallised from 2-propanol m.p. 135°–7° C.

Analysis Found: C, 66.4; H, 6.7; N, 10.7%; C$_{19}$H$_{19}$N$_3$O$_3$.C$_3$H$_8$O requires: C, 66.5; H, 6.8; N, 10.6%.

PREPARATION 3

3-[2-(1,3-Dihydro-1,3-dioxo-2H-isoindol-2yl)ethyl]-1H-indole-5-carbonitrile (i) 4-[2-[4-(1,3-Dihydro-1,3-dioxo-2H-isoindol-2-yl) butylidine]hydrazino]benzonitrile.

A solution of 4-[1,3-dihydro-1,3-dioxo-2H-isoindol-2-yl]-butanal diethyl acetal (13.7 g) in ethanol (100 ml) was added dropwise to a suspension of 4-cyanophenylhydrazine hydrochloride (8 g) in aqueous acetic acid (50%) at 80° C. After 1 hour the solvent was evaporated off and the residue was triturated with water (200 ml). The solid produced was filtered off, washed with water and was dried, (13.4 g) m.p. 129°–132° C. Crystallisation from ethanol gave a sample m.p. 132°–134° C.

Analysis Found: C, 68.5; H, 5.0; N, 16.3%; C$_{19}$H$_{18}$N$_4$O$_2$ requires: C, 68.5: H, 4.8; N, 16.75%.

(ii) 3-[2-(1,3-Dihydro-1,3-dioxo-2H-isoindol-2-yl) ethyl]-1H-indole-5-carbonitrile, compound with water (4:1)

The crude 4-[2-[4-(1,3-dihydro-1,3-dioxo-2H-isoindol-2-yl)butylidene]hydrazine]benzonitrile (8 g) was added to polyphosphoric acid ethyl ester (40 g) in chloroform (200 ml), and the resulting mixture was heated under reflux for 16 hours. The chloroform was evaporated off and the oily residue was partitioned between aqueous 2 N sodium carbonate solution (150 ml) and ethyl acetate (150 ml). The aqueous layer was extracted with ethyl acetate (2×30 ml) and the combined organic extracts were washed (H$_2$O), dried (MgSO$_4$) and evaporated. Trituration of the residue with ethanol produced a yellow powder (2.1 g) which was filtered off. The filtrate was evaporated and the residual orange oil was chromatographed on silica (Merck 60 mesh). Elution with light petroleum (b.p. 40°–60° C.)-ethyl acetate (1:1) gave the title compound as a pale yellow solid (3.6 g) m.p. 223°–225° C.

Analysis Found: C, 71.65; H, 4.3; N, 12.8%; C$_{19}$H$_{13}$N$_3$O$_2$.0.25H$_2$O requires: C, 71.35; H, 4.25; N, 13.1%.

PREPARATION 4

3-[2-(1,3-Dihydro-1,3-dioxo-2H-isoindol-2-yl)ethyl]-1H-indole-5-carbonitrile (i)
2-[2-(5-Bromo-1H-indol-3-yl)ethyl]-1H-isoindole-1,3(2H)-dione 4-[1,3-Dihydro-1,3-dioxo-2H-isoindol-2-yl]butanal diethyl acetal (11.6 g) was added with vigorous stirring to a solution of 4-bromophenylhydrazine hydrochloride (9.0 g) in 50% aqueous acetic acid (370 ml). The mixture was heated on a steam bath for 4 hours and was then diluted with water, while still hot, to 1 l. The mixture was cooled and an orange yellow precipitate was filtered off and dried in vacuo. The solid was boiled in ethanol (250 ml) for 1 hour and residual solid filtered off and dried to afford the title compound as a yellow solid (9.5 g) m.p. 206°–209° C. Crystallisation of a portion of this solid (0.5 g) from ethanol (25 ml) gave a sample (0.25 g) m.p. 208°–212° C.

Analysis Found: C, 58.5; H, 3.75; N, 7.6%;
$C_{18}H_{13}BrN_2O_2$ requires: C, 58.55; H, 3.55; N, 7.6%.

(ii) 3-[2-(1,3-Dihydro-1,3-dioxo-2H-isoindol-2-yl)ethyl]-1H-indole-5-carbonitrile A mixture of 2-[2-(5-bromo-1H-indol-3-yl) ethyl]-1H-isoindole-1,3(2H)-dione (4.0 g), cuprous cyanide (1.1 g) and N-methyl-2-pyrrolidinone (10 ml) was heated at reflux for 1 hour. The reaction mixture was poured onto ice (30 g) and concentrated ammonia (15 ml) was added and the suspension was stirred for 0.75 hour. The solid was filtered off, washed with water and methanol and was crystallised from aqueous acetone to give the title compound (2.7 g) as a fawn solid m.p. 217°–221° C. T.L.C. Silica ether $R_f$ 0.44.

PREPARATION 5

[2-[5-[[[(Diphenylamino)carbonyl]oxy]carbonyl]-1H-indol-3-yl]ethyl]carbamic acid, phenylmethyl ester A solution of 1-[(diphenylamino)carbonyl]-pyridinium chloride (1.1 g) in water (10 ml) was added rapidly to a stirred solution of 3-[2-[[(phenylmethoxy)carbonyl]amino]ethyl]-1H-indole-5-carboxylic acid (1 g) and triethylamine (0.6 ml) in water (15 ml). After 0.5 hour, an amorphous yellow solid (1.7 g) was filtered off. A sample (0.5 g) was crystallised from a mixture of ethyl acetate and cyclohexane to give the title compound (0.3 g) as a cream crystalline solid m.p. 137°–138.5° C.

Analysis Found: C, 72.0; H, 5.1; N, 7.75%; $C_{32}H_{27}N_3O_5$ requires: C, 72.05; H, 5.1; N, 8.0%.

PREPARATION 6

3-(2-Aminoethyl)-1H-indole-5-carboxylic acid, methyl ester, hydrochloride

Thionyl chloride (25 ml) was added to Analar methanol (84 ml) at 0° C. over a period of 1 hour under nitrogen. 3-(2-Aminoethyl)-1H-indole-5-carboxylic acid hydrochloride (2.5 g) in Analar methanol (35 ml) was added at 0° C. and the mixture was heated at reflux under nitrogen for 2.5 hour, cooled to ca. 45° C. and dry diethyl ether (200 ml) was added. The mixture was cooled and left overnight at 0° C. giving the title compound (1.9 g) as white microcrystals m.p. 265.5°–267° C. T.L.C. Silica, ethyl acetate:2-propanol:water:ammonia (25:15:8:2) $R_f$ 0.46.

Analysis Found: C, 56.8: H, 5.9: N, 11.0%; $C_{12}H_{14}N_2O \cdot HCl$ requires: C, 56.6: H, 5.9: N, 11.0%.

PREPARATION 7

Amberlite Resin (IRA 400 OH$^-$)

Amberlite Resin (IRA 400 Cl$^-$) (20 g) was stirred at room temperature for 1 hour in aqueous sodium hydroxide (2 N, 150 ml) and then allowed to stand overnight. The mixture was filtered and the resin washed with water (50 ml). This resin was used in some of the following Examples.

PREPARATION 8

3-[2-(1,3-Dihydro-1,3-dioxo-2H-isoindol-2-yl)ethyl]-1H-indole-5-carboxamide (i) 3-[2-(1,3-Dihydro-1,3-dioxo-2H-Isoindol-2-yl)ethyl]-1H-indole-5-carboxylic acid, 4-nitrophenyl ester Polyphosphoric acid ethyl ester (40 ml) and 4-nitrophenol (6.3 g) were added to a solution of 3-[2-(1,3-dihydro-1,3-dioxo-2H-isoindol-2-yl)ethyl]-1H-indole-5-carboxylic acid (15 g) in dimethylformamide (70 ml) and the mixture was stirred at 80° C. for 24 hours. More polyphosphoric acid ethyl ester (20 ml) was added and the mixture stirred at 80° C. for 3 hours. The mixture was cooled, poured into ice and water (900 ml) and stirred for 1 hour with ice cooling. The resulting solid was filtered off and washed with boiling ethanol (1500 ml) and hot water (600 ml) to give the title compound (12.5 g) as pale yellow crystals m.p. 248°–251° C. T.L.C. Silica, ethyl acetate:2-propanol:water:ammonia (25:15:8:2) $R_f$ 0.9.

(ii) 3-[2-(1,3-Dihydro-1,3-dioxo-2H-isoindol-2-yl)ethyl]-1H-indole-5-carboxamide Ammonia (0.88, 0.2 ml) was added to a solution of 3-[2-(1,3-dihydro-1,3-dioxo-2H-isoindol-2-yl) ethyl]-1H-indole-5-carboxylic acid, 4-nitrophenyl ester (0.3 g) in warm (50° C.) dimethylformamide (3 ml). The mixture was stirred at 50° C. for 4 hours., poured into water (40 ml) and stirred for a further 0.5 hours. The precipitate (0.21 g) was collected and crystallised from ethanol to give the title compound (0.12 g) as an off-white solid m.p. 254°–6° C. T.L.C. Silica, Ethyl acetate:2-propanol:water:ammonia (25:15:8:2) $R_f$ 0.75.

EXAMPLE 1

(i)a [2-[5-[[(Phenylmethyl)amino]carbonyl]1H-indol-3-yl]ethyl]carbamic acid, phenylmethyl ester, quarter hydrate Triethylamine (3.6 ml) was added to a stirred mixture of 2-chloro-1-methylpyridinium iodide (4.5 g) and 3-[2-[[(phenylmethoxy)carbonyl]amino]ethyl]-1H-indole-5-carboxylic acid (3.0 g) in dry acetonitrile (200 ml). After 1 hour at room temperature, benzylamine (3.9 ml) was added and stirring was continued for a further 24 hours. The solvent was evaporated in vacuo and the residue partitioned between ethyl acetate (200 ml) and sodium hydroxide (1 N, 250 ml). The aqueous phase was further extracted with ethyl acetate (2×100 ml) and the combined extracts were washed with sodium hydroxide (1 N, 100 ml), sulphuric acid (1 N, 2×150 ml) and brine (200 ml), dried (Na$_2$SO$_4$) and evaporated in vacuo to give a dark oil (3.7 g), which after treatment with a mixture of methanol and ethyl acetate gave the title compound as an off-white solid (1.2 g) m.p. 129°–130.5° C.

Analysis Found: C, 72.2; H, 5.8; N, 9.6%; $C_{26}H_{25}N_3O_3 \cdot \frac{1}{4}H_2O$ requires: C, 72.3; H, 5.9; N, 9.7%.

The following compounds were similarly prepared from 3-[2-[[(phenylmethoxy)carbonyl]amino]ethyl]-1H-indole-5-carboxylic acid (A) and the appropriate amine:

(i)b 2-propylamine (2 ml) and A (1.0 g) gave [2-[5-[[(1-methylethyl)amino]carbonyl]-1H-indol-3-yl]ethyl]carbamic acid, phenylmethyl ester (0.45 g) m.p. 136°–7° C. (from ethyl acetate).

Analysis Found: C, 69.1; H, 6.7; N, 11.1%; $C_{22}H_{25}N_3O_3$ requires: C, 69.6; H, 6.6; N, 11.1%.

(i)c Morpholine (3 ml) and A (2.5 g) gave [2-[5-[(4-morpholinyl)carbonyl]-1H-indol-3-yl]ethyl]carbamic acid, phenylmethyl ester (1.7 g) as light brown foam. T.L.C. silica, ethyl acetate:cyclohexane 1:1 $R_f$ 0.36.

(i)d Aniline (5.4 ml) and A (10.0 g) gave [2-[5-[(phenylamino)carbonyl]-1H-indol-3-yl]ethyl]carbamic acid, phenylmethyl ester (1.3 g) m.p. 136.5°–137.5° C. from ethyl acetate:petroleum ether (b.p. 40°–60° C.)] after purification on a silica column (Kieselgel 60, 400 g) eluted with chloroform containing 5% methanol.

Analysis Found: C, 72.1; H, 5.4; N, 9.7% $C_{25}H_{23}N_3O_3$ requires: C, 72.6; H, 5.6; N, 10.2%

(i)e Cyclopentylamine (1.2 ml) and A (2.0 g) gave [2-[5-[(cyclopentylamino)carbonyl]-1H-indol-3-yl]ethyl]carbamic acid, phenylmethyl ester hemihydrate (1.2 g) m.p. 165°–7° C.

Analysis Found: C, 70.4; H, 6.6; N, 10.3%; $C_{24}H_{27}N_3O_3.\frac{1}{2}H_2O$ requires: C, 70.3; H, 6.8; N, 10.25%.

(i)f 2-Methoxyethylamine (0.8 ml) and A (3.0 g) gave [2-[5-[[(2-methoxyethyl)amino]carbonyl]-1H-indol-3-yl]ethyl]carbamic acid, phenylmethyl ester (2.3 g) as a yellow oil after purification by chromatography on a silica column (Kieselgel 60, 60 g) eluted with ethyl acetate. T.L.C. silica, ethyl acetate $R_f$ 0.25.

(ii)a
3-(2-Aminoethyl)-N-(phenylmethyl)-1H-indole-5-carboxamide, compound with creatinine, sulphuric acid and water (1:1:1)

A solution of [2-[5-[[(phenylmethyl)amino]carbonyl]-1H-indol-3-yl]ethyl]carbamic acid, phenylmethyl ester, quarter hydrate (0.8 g) in ethanol (40 ml) was hydrogenated at room temperature and pressure over palladium oxide on charcoal (10%; 400 mg; prereduced) until hydrogen uptake ceased. The mixture was filtered through a Hyflo (diatomaceous earth) pad and the filtrate evaporated in vacuo to give a dark yellow oil (0.8 g). A portion (0.6 g) of the oil was dissolved in hot ethanol (10 ml) and a solution of creatinine sulphate in water (2 M; 1:1; 1.5 ml) was added. The precipitate that formed was filtered off and crystallised from aqueous ethanol to give the title compound (0.21 g) as a white solid m.p. 206°–8° C.

Analysis Found: C, 50.2; H, 5.5; N, 16.2%; $C_{18}H_{19}N_3O.C_4H_7N_3O.H_2SO_4.H_2O$ requires: C, 50.6; H, 5.7; N, 16.1%.

The following compounds were similarly prepared by hydrogenation of the intermediates stated followed by formation of the appropriate salt:

(ii)b [2-[5-[[(1-Methylethyl)amino]carbonyl]1H-indol-3-yl]ethyl carbamic acid, phenylmethyl ester (0.4 g) gave 3-(2-aminoethyl)-N-(1-methylethyl)-1H-indole-5-carboxamide, maleate (0.25 g) as a white crystalline solid m.p. 174°–5° C. (from methanol/ethyl acetate)

Analysis Found: C, 59.8; H, 6.4; N, 11.6%; $C_{14}H_{19}N_3O.C_4H_4O_4$ requires: C, 59.8; H, 6.4; N, 11.6%.

(ii)c [2-[5-[(4-Morpholinyl)carbonyl]-1H-indol-3-yl]ethyl]carbamic acid, phenylmethyl ester (1.5 g) gave 4-[[3-(2-aminoethyl)-1H-indol-5-yl]carbonyl] morpholine, compound with creatinine, sulphuric acid and water (1:1:1:1) (0.65 g) as a white crystalline solid m.p. 178°–181° C. (from aqueous ethanol)

Analysis Found: C, 45.7; H, 5.7; N, 16.4%; $C_{15}H_{19}N_3O_2.C_4H_7N_3O.H_2SO_4.H_2O$ requires: C, 45.4; H, 6.0; N, 16.7%.

(ii)d [2-[5-[(Phenylamino)carbonyl]-1H-indol-3-yl]ethyl]carbamic acid, phenylmethyl ester (1.06 g) gave 3-(2-aminoethyl)-N-phenyl-1H-indole-5-carboxamide hydrochloride (0.23 g) as a white crystalline solid m.p. 261.5°–263° C. (from methanol/ethyl acetate)

Analysis Found: C, 64.6: H, 5.8; N, 13.0%; $C_{17}H_{17}N_3O.HCl$ requires: C, 64.7; H, 5.4; N, 13.3%.

(ii)e [2-[5-[(Cyclopentylamino)carbonyl]-1H-indol-3-yl]ethyl]carbamic acid, phenylmethyl ester (0.9 g) gave 3-(2-aminoethyl)-N-cyclopentyl-1H-indole-5-carboxamide, quarter hydrate as an off-white solid (0.6 g) m.p. 222°–223° C. (dec.)

Analysis Found: C, 69.4; H, 8.0; N, 15.2%; $C_{16}H_{21}N_3O.\frac{1}{4}H_2O$ requires: C, 69.7; H, 7.7; N, 14.7%.

(ii)f [2-[5-[[(2-Methoxyethyl)amino]carbonyl]-1H-indol-3-yl]ethyl]carbamic acid, phenylmethyl ester (2.0 g) gave 3-(2-aminoethyl)-N-(2-methoxyethyl)-1H-indole-5-carboxamide, compound with creatinine, sulphuric acid and water (1:1:1:2) (0.8 g) as a white crystalline solid m.p. 193°–5° C. (from aqueous ethanol)

Analysis Found: C, 42.7; H, 6.1; N, 16.7%; $C_{14}H_{19}N_3O_2.C_4H_7N_3O.H_2SO_4.2H_2O$ requires: C, 42.5; H, 6.3; N, 16.5%.

EXAMPLE 2

3-(2-Aminoethyl)-N-(4-methoxyphenyl)-1H-indole-5-carboxamide, hydrate (i)
[2-[5-[[(4-Methoxyphenyl)amino]carbonyl]-1H-indol-3-yl]ethyl]carbamic acid, phenylmethyl ester A mixture of [2-[5-[[[(diphenylamino)carbonyl]oxy]carbonyl]-1H-indol-3-yl]ethyl]carbamic acid, phenylmethyl ester (2.5 g) and 4-methoxyaniline (3.0 g) was heated at 100° C. for 0.25 hour, and the resulting liquid was partitioned between hydrochloric acid (1 N; 100 ml) and ethyl acetate (100 ml). The organic layer was washed successively with hydrochloric acid (1 N; 100 ml), sodium bicarbonate solution (8%; 2×100 ml), and brine (2×100 ml), dried (magnesium sulphate), and evaporated in vacuo affording a red solid (2.6 g). The solid was triturated with ether (150 ml) to give a pale red solid (1.6 g) which was purified by chromatography on a silica column (Kieselgel 60; 40 g) eluted with chloroform-methanol (99:1) to give the title compound as an off-white solid (1.28 g). T.L.C. Silica, chloroform:methanol (39:1) $R_f$ 0.25

Analysis Found: C, 70.6; H, 5.7; N, 9.5%; $C_{26}H_{25}N_3O_4$ requires: C, 70.4; H, 5.7; N, 9.5%.

(ii)
3-(2-Aminoethyl)-N-(4-methoxyphenyl)-1H-indole-5-carboxamide, hydrate

Following the method of Example 1(ii) a [2-[5-[[(4-methoxyphenyl)amino]carbonyl]-1H-indol-3-yl]ethyl]carbamic acid, phenylmethyl ester (0.725 g) was hydrogenated to give an orange oil which crystallised on standing. Trituration with dry ether gave the title amide as an off-white crystalline solid (0.25 g) m.p. 163°–6° C. (dec.)

Analysis Found: C, 66.5; H, 6.0; N, 12.5%; $C_{18}H_{19}N_3O_2.H_2O$ requires: C, 66.0; H, 6.5; N, 12.8%.

EXAMPLE 3

3-(2-Aminoethyl)-N-(2,2,2-trifluoroethyl)-1H-indole-5-carboxamide, compound with creatinine, sulphuric acid and water (2:2:2:3)

(i)
[2-[5-[[(2,2,2-Trifluoroethyl)amino]carbonyl]-1H-indol-3-yl]ethyl]carbamic acid, phenylmethyl ester A mixture of [2-[5-[[[(diphenylamino)carbonyl]oxy]carbonyl]-1H-indol-3-yl]ethyl]carbamic acid, phenylmethyl ester (0.5 g) and 2,2,2-trifluoroethylamine (0.4 ml) was heated at 100° C. for 10 mins. in an autoclave. The mixture was cooled in an ice bath and triturated with cyclohexane (70 ml) to give a cream solid (0.3 g) which was crystallised from ethyl acetate and cyclohexane to give the title compound as an off-white crystalline solid (0.2 g) m.p. 138°–140° C.

Analysis Found: C, 59.6; H, 4.7; N, 9.7%; $C_{21}H_{20}F_3N_3O_3$ requires: C, 60.1; H, 4.8; N, 10.0%.

(ii)

3-(2-Aminoethyl)-N-(2,2,2-trifluoroethyl)-1H-indole-5-carboxamide, compound with creatinine, sulphuric acid and water (2:2:2:3)

Following the method of Example 1(ii) a [2-[5-[[(2,2,2-trifluoroethyl)amino]carbonyl]-1H-indol-3-yl]ethyl]carbamic acid, phenylmethyl ester (0.5 g) was hydrogenated and the product converted to the creatinine sulphate salt to give the title compound (0.5 g) as a white crystalline solid m.p. 234°–7° C. (dec.) (from aqueous ethanol)

Analysis Found: C, 38.7; H, 4.9; N, 15.9%; $C_{13}H_{14}F_3N_3O.C_4H_7N_3O.H_2SO_4.1\frac{1}{2}H_2O$ requires: C, 39.0: H, 5.0; N, 16.05%.

EXAMPLE 4

3-(2-Aminoethyl)-N-(prop-2-enyl)-1H-indole-5-carboxamide, hydrobromide, hemihydrate (i)

[2-[5-[(prop-2-enylamino)carbonyl]-1H-indol-3-yl]ethyl]carbamic acid, phenylmethyl ester, quarter hydrate A mixture of [2-[5-[[[(diphenylamino)carbonyl]oxy]-carbonyl]-1H-indol-3-yl]ethyl]carbamic acid, phenylmethyl ester (1.0 g) and allylamine (1 ml) was stirred at room temperature for 1 hour. The excess allylamine was removed by evaporation under reduced pressure and the residue triturated with dichloromethane (10 ml). The resulting solid was filtered off, washed with diethyl ether and dried to give the title compound (0.25 g) as a white solid m.p. 136°–7° C.

Analysis Found: C, 68.95; H, 5.7; N, 11.0%; $C_{22}H_{23}N_3O_3.0.25H_2O$ requires: C, 69.2; H. 6.1; N, 11.0%.

(ii)

3-(2-Aminoethyl)-N-(prop-2-enyl)-1H-indole-5-carboxamide, hydrobromide, hemihydrate

[2-[5-[(Prop-2-enylamino)carbonyl]-1H-indol-3-yl]ethyl]carbamic acid, phenylmethyl ester, quarter hydrate (0.5 g) was treated with hydrogen bromide in glacial acetic acid (45%, 3 ml), at room temperature, with stirring, for 0.33 hour and diluted with diethyl ether (25 ml). The resulting solid was filtered off, washed with ether (3×5 ml) and recrystallised from a mixture of ethanol and cyclohexane to afford the title compound (0.25 g) as a white crystalline solid m.p. 224°–227° C.

Analysis Found: C, 50.55; H, 5.4; N, 12.4%; $C_{14}H_{17}N_3O.HBr.\frac{1}{2}H_2O$ requires: C, 50.5; H, 5.75; N, 12.6%.

EXAMPLE 5

3-(2-Aminoethyl)-N,N-dimethyl-1H-indole-5-carboxamide, compound with creatinine, sulphuric acid and water (2:2:2:3)

[2,[5-[(Dimethylamino)carbonyl]-1H-indol-3-yl]ethyl]-carbamic acid, phenylmethyl ester, hydrate A stirred solution of 3-(2-aminoethyl)-1H-indole-5-carboxylic acid hydrochloride (2.6 g) in dry dimethylformamide (700 ml) was treated with triethylamine (5.0 g) followed by benzyl chloroformate (17.0 g). After 1 hour at room temperature, dimethylamine in ethanol (30%, 50 ml) was added and the yellow solution kept at room temperature for 18 hours before evaporating to small volume (approx. 100 ml). The mixture was poured into water (1 liter), acidified with dilute hydrochloric acid and extracted with ethyl acetate (5×200 ml). The combined extracts were washed with water (5×100 ml), dried ($Na_2SO_4$) and evaporated to dryness to give a yellow oil which was purified on a silica column (Kieselgel 60, 100 g) eluted with ethyl acetate/cyclohexane (1:1) to give the title amide (1.1 g) as a pale yellow foam. T.L.C. Silica, ethyl acetate $R_f 0.35$ Analysis Found: C, 66.0; H, 6.3; N, 10.7%, $C_{21}H_{23}N_3O_3.H_2O$ requires: C, 65.8; H, 6.6; N, 11.0%.

(ii)

3-(2-Aminoethyl)-N,N-dimethyl-1H-indole-5-carboxamide, compound with creatinine, sulphuric acid and water (2:2:2:3)

Following the method of example 1(ii) a [2,-[5-[(dimethylamino)carbonyl]-1H-indol-3-yl[ethyl]carbamic acid, phenylmethyl ester, hydrate (1.0 g) was hydrogenated and the product converted to the creatinine sulphate salt to give the title compound (1.0 g) as a white crystalline solid m.p. 192°–4° C.

Analysis Found: C, 43.5: H, 6.0; N, 18.2%; $C_{13}H_{17}N_3O.C_4H_7N_3O.H_2SO_4.1\frac{1}{2}H_2O$ requires: C, 43.5; H,6.1; N,17.9%.

EXAMPLE 6

3-(2-Aminoethyl)-1H-indole-5-carboxamide, compound with creatinine, sulphuric acid and water (1:1:1:2)

3-(2-Aminoethyl)-1H-indole-5-carboxylic acid, methyl ester, hydrochloride (1.0 g) in ammonia (0.88 d, 50 ml) was heated at 50° C. for 48 hours. The reaction mixture was evaporated in vacuo and the resulting crude oil was purified by chromatography on silica gel (Hopkins & Williams MFC, 50 g). Elution with ethyl acetate:2-propanol: water:ammonia (25:10:8:2) gave the amide (0.86 g) as a colourless oil which was converted into its creatinine sulphate salt in aqueous acetone to give the title compound (0.7 g) as colourless microcrystals m.p. 215°–225° C.(dec.)

Analysis Found: C, 40.9; H, 6.0; N, 19.1%; $C_{11}H_{13}N_3O.C_4H_7N_3O.H_2SO_4.2H_2O$ requires: C, 40.9; H, 5.7; N, 19.1%.

EXAMPLE 7

3-(2-Aminomethyl)-N-methyl-1H-indole-5-carboxamide, hydrochloride 3-(2-Aminoethyl)-1H-indole-5-carboxylic acid, methyl ester, hydrochloride (2 g) was dissolved in aqueous methylamine solution (40%, 100 ml) and stirred at 50°–60° C. under nitrogen for 4.5 hours. The reaction mixture was evaporated to dryness in vacuo and the resulting white solid (2.2 g) was purified by column chromatography on silica gel (40 g). Elution with ethyl acetate: 2-propanol:water:ammonia 25:15:8:2 gave the amide as a pale brown oil (1.2 g) which was converted into the hydrochloride salt with ethereal hydrogen chloride to give the title compound (1.15 g) as white microcrystals m.p. 182°–5° C. T.L.C. Silica ethyl acetate: 2-propanol:water:ammonia (25:15:8:2) $R_f 0.44$.

EXAMPLE 8

3-(2-Aminoethyl)-N-(hydroxyethyl)-1H-indole-5-carboxamide, compound with creatinine, sulphuric acid and water (2:2:2:5)

Following the method of example 6, 3-(2-aminoethyl)-1H-indole-5-carboxylic acid, methyl ester, hydrochloride (0.6 g) was heated with ethanolamine (10 ml) at 75° C. for 24 hours. The product was converted to its creatinine sulphate, salt in aqueous acetone to give the title compound (0.55 g) as colourless microcrystals m.p. 227°–230° C. (foam) softened 173° C.

Analysis Found: C, 40.7; H,6.0;N,17.2%, $C_{13}H_{17}N_3O_2.C_4H_7N_3O.H_2SO_4.2.5H_2O$ requires: C,40.6; H,6.2;N,16.7%.

EXAMPLE 9

(i) a 3-[[Methyl(phenylmethyl)amino]acetyl]-1H-indole-5-carbonitrile 3-(Bromoacetyl)-1H-indole-5-carbonitrile (5.0 g) was added to a solution of methyl benzylamine (4.85 g) in 2-propanol (175 ml) and the mixture was refluxed with stirring under nitrogen for 2.5 hours. The resulting solution was allowed to cool to room temperature overnight. The title compound (4.8 g) crystallised from solution and was collected, washed with 2-propanol and ether, and dried m.p. 195°–205° C. A portion of the product was recrystallised from 2-propanol to afford colourless needles m.p. 200°–205° C.

Analysis Found: C, 74.9; H, 5.6; N, 13.6%, $C_{19}H_{17}N_3O$ requires: C, 75.2; H, 5.6; N, 13.85%.

The following compounds were similarly prepared from 3-(bromoacetyl)-1H-indole-5-carbonitrile(A) and the appropriate amine:

(i)b Di-n-propylamine (8 ml) and A (5 g) gave 3-[(dipropylamino)acetyl]-1H-indole-5-carbonitrile (5 g) as a yellow solid. T.L.C. Silica, ethyl acetate: methanol (19:1) $R_f$0.17.

(i)c Piperazine (1.0 g) and A (3.0 g) gave 3-[1-piperazinyl)acetyl]-1H-indole-5-carbonitrile (1.85 g)m.p. 241°–273° C. (dec.). T.L.C. Silica, ethyl acetate: 2-propanol:water:ammonia (25:15:8:2) $R_f$0.38.

(i)d 2,2,2-Trifluoroethylamine (3.0 ml), A (1.0 g) and butanone (30 ml) at 100° C. in an autoclave for 3.75 hours gave 3-[(2,2,2-trifluorethylamino)acetyl]-1H-indole-5-carbonitrile, hydrobromide, hemihydrate (1.22 g) m.p. 248°–253° C. (dec.).

Analysis Found: C, 42.2; H, 3.2; N, 11.1%, $C_{13}H_{10}F_3N_3O.HBr.O.5H_2O$ requires: C, 42.1; H, 3.3; N, 11.3%.

(ii)a 3-[2-[Methyl)phenylmethyl)amino[ethyl]-1H-indole-5-carbonitrile

A mixture of 3-[[methyl(phenylmethyl)amino]acetyl]-1H-indole-5-carbonitrile (4.5 g) and sodium borohydride (10.0 g) in 1-propanol (200 ml) was refluxed under nitrogen for 2 hours. The resluting white paste was cooled to room temperature and then treated with a mixture of ethyl acetate (200 ml) and water (200 ml). The aqueous layer was separated and extracted with ethyl acetate (2×200 ml). The combined ethyl acetate solutions were then extracted with 2 N hydrochloric acid (3×250 ml). The acid extracts were basified to pH 14 with 2 N sodium hydroxide with ice-bath cooling and then extracted with ethyl acetate (3×200 ml). The combined extracts were dried (MgSO₄), filtered and evaporated in vacuo to give an oil (2.7 g). Evaporation of the ethyl acetate solution which had been extracted with aqueous acid gave a further quantity of impure material (2.1 g). Chromatography of the combined products on silica gel (60 mesh; 200 g) with a mixture of ethyl acetate; 2-propanol (10:1) as eluent gave the title compound (2.0 g) as a yellow crystalline solid m.p. 77°–81.5° C.

Analysis Found: C, 78.6; H, 6.7; N, 14.4%, $C_{19}H_{19}N_3$ requires: C, 78.9, H, 6.6; N, 14.5%. The following compounds were similarly prepared by reduction of the intermediates (i)b-d with sodium borohydride (ii)b 3-[(Dipropylamino)acetyl]-1H-indole-5-carbonitrile (4.5 g) and sodium borohydride (11 g) gave 3-[2-(dipropylamino)ethyl]-1H-indole-5-carbonitrile, hydrochloride, hemihydrate (1.07 g) m.p. 204°–5° C.

Analysis Found: C, 65.0; H, 8.2; N, 13.3%; $C_{17}H_{23}N_3.HCl.0.5H_2O$ requires: C, 64.95; H, 8.0; N, 13.4%

(ii)c 3-[(1-Piperazinyl)acetyl]-1H-indole-5-carbonitrile (1.85 g) and sodium borohydride (2.85 g) gave 3-[2-(1-piperazinyl)ethyl]-1H-indole-5-carbonitrile (1.1 g) as a brown oil. A portion of this material was converted into its maleate salt (97 mg) as a colourless crystalline solid m.p. 95°–97° C.

Analysis Found: C, 52.8; H, 5.4; N, 10.4%; $C_{15}H_{18}N_4.2C_4H_4O_4.2H_2O$ requires: C, 52.85; H, 5.8; N, 10.7%

(ii)d 3-[(2,2,2-Trifluoroethylamino)acetyl]-1H-indole-5-carbonitrile (0.85 g) (obtained from the hydrobromide (1.19 g) and sodium borohydride (2.1 g) gave 3-[2-(2,2,2-trifluoroethylamino)ethyl]-1H-indole-5-carbonitrile (0.64 g) m.p. 102.4° C. T.L.C. Silica, ethyl acetate $R_f$0.48

(iii)a 3-[2-[Methyl(phenylmethyl)amino]ethyl]-1H-indole-5-carboxamide, compound with creatinine, sulphuric acid, acetone, ethanol and water (20:20:20:12:1)

A mixture of 3-[2-[methyl(phenylmethyl)amino]ethyl]-1H-indole-5-carbonitrile (2.5 g), Amberlite resin (Preparation 7, 20 g) and water (50 ml) was refluxed for 10 hours. The cooled mixture was filtered and the resin thoroughly washed with hot ethanol (200 ml). The combined solutions were evaporated to afford an oil (1.35 g) which solidified in vacuo.

Analysis Found: C, 74.55, H, 7.2; N, 13.25%; $C_{19}H_{21}N_3O$ requires: C, 74.25; H, 6.9; N, 13.65% T.L.C. Silica, ethanol $R_f$0.65

The following compounds were similarly prepared by hydrolysis of the intermediates (ii)b-d with Amberlite resin (Preparation 7) followed by formation of the appropriate salt.

(iii)b 3-[2-(Dipropylamino)ethyl]-1H-indole-5-carbonitrile (2.3 g) and Amberlite resin (60 g) gave a gummy oil (1.05 g) which crystallised from a mixture of ethyl acetate and ether to give 3-[2-dipropylamino)ethyl]-1H-indole-5-carboxamide, quarter hydrate (0.288 g) as a colourless crystalline solid m.p. 157°–8° C.

Analysis Found: C, 69.8; H, 8.65; N, 14.35%; $C_{17}H_{25}N_3O.0.25H_2O$ requires: C, 69.95; H, 8.8; N, 4.4%, (iii)c 3-[2-(1-Piperazinyl)ethyl]-1H-indole-5-carbonitrile (0.4 g) and Amberlite resin (4 g) gave 3-[2-(1-piperazinyl)-ethyl]-1H-indole-5-carboxamide, dimaleate, hemihydrate (0.09 g) as a brown crystalline solid m.p. 151°–154° C. (dec.) T.L.C. Silica, ethyl acetate: 2-propanol:water:ammonia (25:18:8:2) $R_f$0.3

(iii)d A stirred suspension of 3-[2-(2,2,2-trifluoroethylamino)ethyl]-1H-indole-5-carbonitrile (0.599 g) and Amberlite resin (10 g) in water (50 ml) was heated at reflux for 18.5 hours. The mixture was filtered hot and the filtrate was evaporated to dryness. The resulting white solid was extracted into hot methanol (4×50 ml) which was evaporated to give the amide as a pale yellow oil (0.19 g). This was dissolved in ethyl acetate (25 ml), diluted with dry ether (25 ml) and treated with ethereal hydrogen chloride to give 3-[2-(2,2,2-trifluoroethylamino)ethyl]-1H-indole-5-carboxamide, hydrochloride, 1.25 hydrate as an amorphous off-white solid (0.15 g) m.p. 225°–9° C. (dec).

Analysis Found: C, 45.25; H, 4.7; N, 11.8%; $C_{13}H_{14}F_3N_3O.HCl.1.25H_2O$ requires: C, 45.35; H, 5.1; N, 12.2%;

(iii)e  3-[2-(4-Morpholinyl)ethyl]-1H-indole-5-carboxamide

A stirred mixture of 3-[2-(4-morpholinyl)ethyl]-1H-indole-5-carbonitrile (1.0 g), Amberlite resin (10 g) and water (30 ml) was heated at reflux under nitrogen for 4 hours. The reaction mixture was filtered and the resin was washed with hot water (50 ml). The aqueous solution was allowed to cool to room temperature to give the title compound (0.3 g) as a colourless solid m.p. 205°–206.5° C.

Analysis Found: C, 65.9; H, 7.1; N, 15.4%; $C_{19}H_{19}N_3O_2$ requires: C, 65.9; H, 7.1; N, 15.4%;

(iii)f  3-[2-(Dimethylamino)ethyl]-1H-indole-5-carboxamide compound with creatinine, sulphuric acid, water, ethanol and acetone (1:1:1:2:0.25:0.18)

A mixture of 3-[2-(dimethylamino)ethyl]-1H-indole-5-carbonitrile (0.7 g) water (30 ml) and Amberlite resin (20 g) was heated under reflux for 18 hours. The resin was filtered and the filtrate evaporated to give an oil which was dissolved in a mixture of methanol and ethyl-acetate (1:2; 15 ml), filtered and evaporated to give a yellow oil (0.22 g). The resin was continuously extracted with ethanol (150 ml) for 2 hours and the extract was evaporated to afford a further 0.1 g of crude product.

Column chromatography on silica gel (60–120 mesh, 15 g) using ethyl acetate: 2-propanol; water: 0.88 ammonia (25:15:4:1) as eluent gave a yellow oil (0.17 g). Conversion of the oil into its creatinine sulphate salt gave the title compound (0.27 g) as a colourless crystalline solid m.p. 115°–120° C. (dec.). T.L.C. Silica, ethyl acetate: 2-propanol:water:ammonia (25:15:8:2) $R_f$ 0.5

EXAMPLE 10

(a)

3-[2-(1-Methyl-2-phenylethyl)amino]ethyl]-1H-indole-5-carboxamide

A mixture of [2-[5-(aminocarbonyl)-1H-indol-3-yl]-ethyl]carbamic acid, phenylmethyl ester (1 g), phenyl acetone (2 ml) and palladium on carbon (10%, 0.2 g) in ethanol (50 ml) was stirred under a hydrogen atmosphere for 18 hours. The catalyst was filtered off and the filtrate was evaporated to dryness. Trituration of the residue will ether gave the title compound as a white micro-crystalline solid (0.45 g) m.p. 150°–152° C.

Analysis Found: C, 74.5 H, 7.15; N, 12.75%; $C_{20}H_{23}N_3O$ requires: C, 74.75; H, 7.15; N, 13.1%.

(b)

3-[2-[1-Methyl-4-phenylbutyl)amino]ethyl]-1H-indole-5-carboxamide

Was prepared in a similar manner to that described in Example 10a from [2-[[5-(aminocarbonyl)-1H-indol-3-yl]ethyl]carbamic acid, phenylmethyl ester (1.0 g), palladium on carbon (10%, 0.5 g) and 5-phenylpentan-2-one (5 ml) to give the title compound (0.4 g) as a colourless crystalline solid, m.p. 146°–9° C. after purification on a silica column (Kieselgel 60 mesh, 100 g) eluted with a mixture of ethyl acetate:2-propanol:water-:ammonia (25:15:8:2) and crystallisation from a mixture of ethyl acetate and light petroleum (b.p. 60°–80° C.).

Analysis Found: C, 75.2; H, 7.65; N, 11.8%; $C_{22}H_{27}N_3O$ requires: C, 75.6; H, 7.8; N, 12.05%.

(c)

3-[2-(Dimethylamino)ethyl]-N-(hydroxymethyl)-1H-indole-5-carboxamide, compound with ethanol (10:1)

A mixture of [2-[5-(aminocarbonyl)-1H-indol-3-yl]-ethyl]carbamic acid, phenylmethyl ester (3.0 g) aqueous formaldehyde (36%, 20 ml) and palladium oxide on charcoal 10%, 1.6 g) in ethanol (200 ml) was hydrogenated at room temperature and 45 p.s.i. for 24 hours. The catalyst was filtered off and the filtrate evaporated to give a white paste which was purified on a silica column (Kieselgel 60, 200 g) eluted with ethy acetate:2-propanol:water:ammonia (25:15:4:1) to give a pink, waxy solid (1.2 g). This material was triturated with boiling acetone to give the title compound (0.44 g) m.p. 148°–151° C.

Analysis Found: C, 64.05; H, 7.6; N, 15.9%; $C_{14}H_{19}N_3O_2.0.1C_2H_6O$ requires: C, 64.1; H, 7.5; N, 15.9%.

EXAMPLE 11

(a)

3-[2-[(1-Methyl-3-phenylpropyl)amino]ethyl]-1H-indole-5-carboxamide, compound with water (4:1)

A solution of 3-(2-aminoethyl)-1H-indole-5-carboxamide (0.5 g) in ethanol (100 ml) containing benzyl acetone (2 ml) was stirred over pre-reduced palladium oxide on carbon catalyst (10%, 0.5 g) under a hydrogen atmosphere at room temperature and atmospheric pressure. After 16 hours the catalyst was filtered off and the filtrate was evaporated in vacuo. The resulting oil was dissolved in ethyl acetate (20 ml), and was added dropwise to rapidly-stirred light petroleum (b.p. 40°–60° C.) (80 ml). A finely divided white amorphous solid precipitated and was collected and dried (0.8 g). Reprecipitation using the same volumes of ethyl acetate and light petroleum (b.p. 40°–60° C.) afforded the title compound as a white solid (0.51 g) m.p. 110°–117° C.

Analysis Found: C, 74.3; H, 7.7; N, 12.6% $C_{21}H_{25}N_3O.\frac{1}{4}H_2O$ requires: C, 74.6; H, 7.6; N, 12.4%.

(b)

3-[2-[(1-Methylethyl)amino]ethyl]-1H-indole-5-carboxamide, compound with creatinine, sulphuric acid and water (4:4:4:5)

In a similar manner to that described in Example 11a, 3-(2-aminoethyl)-1H-indole-5-carboxamide (0.4 g) and acetone (10 ml) were hydrogenated in ethanol (150 ml) at 40 p.s.i. for 4 hours to give, after conversion into the creatinine sulphate salt, the title compound (0.27 g) as a colourless crystalline solid m.p. 220°–228° C. (dec.,)

Analysis Found: C, 44.8; H, 6.3; N, 17.65% $C_{14}H_{19}N_3O.C_4H_7N_3O.H_2SO_4.1.25H_2O$ requires: C, 45.15; H, 6.4; N, 17.55%.

EXAMPLE 12

3-[2-[[3-(4-Chlorophenyl)-1-methylpropyl]amino]ethyl]-1H-indole-5-carboxamide, compound with maleic acid and water (1:1:1)

A mixture of 3-(2-aminoethyl)-1H-indole-5-carboxamide (0.7 g), 4-(4-chlorophenyl)butan-2-one (1 ml) and sodium cyanoborohydride (0.31 g) in methanol (30 ml) was kept at 20° C. for 4 days. The solution was maintained at pH 6 by addition of aqueous 2 N hydrochloric acid solution. Excess ethereal hydrogen chloride was added and the solid produced was filtered off and discarded. The filtrate was evaporated to dryness and the residue was made basic with concentrated aqueous ammonia (10 ml). The mixture was extracted with ethyl acetate 3×30 ml) and evaporation of the washed (H$_2$O) and dried (MgSO$_4$) organic extracts gave a pale yellow gum. The gum was redissolved in absolute ethanol (10 ml) and maleic acid (0.5 g) was added. Addition of dry ether (100 ml) afforded the title compound (0.27 g) as a pale yellow solid. m.p. 126°–130° C.

Analysis Found: C, 59.75; H, 5.65; N, 8.6% C$_{21}$H$_{24}$ClN$_3$O.C$_4$H$_4$O$_4$.H$_2$O requires: C, 59.6; H, 5.95; N, 8.35%.

EXAMPLE 13

3-[2-(Phenylmethylamino)ethyl]-1H-indole-5-carboxamide, compound with creatinine, sulphuric acid, ethanol and water (3:5:4:2:6)

(i) 3-[2-(Phenylmethylideneamino)ethyl]-1H-indole-5-carboxamide, compound with water (4:3)

Freshly distilled benzaldehyde (0.6 g) in benzene (3 ml) was added to 3-(2-aminoethyl)-1H-indole-5-carboxamide (1.2 g) at room temperature. A gummy oil separated out and the mixture was stirred manually for 15 min. before being left at room temperature overnight. The mixture was evaporated to an orange gum which was triturated with an ether-benzene mixture (1:1, 200 ml) to give the title compound as an off-white solid (1.1 g) m.p. 152°–157° C.

Analysis Found: C, 71.0; H, 6.0; N, 13.8% C$_{18}$H$_{17}$N$_3$O,$\frac{3}{4}$H$_2$O requires: C, 70.9; H, 6.1; N, 13.8%.

(ii) 3-[2-(phenylmethylamino)ethyl]-1H-indole-5-carboxamide, compound with creatinine, sulphuric acid, ethanol and water (3:5:4:2:6)

Sodium borohydride (0.05 g) was added with stirring to a solution of 3-[2-(phenylmethylideneamino)ethyl]-1H-indole-5-carboxamide (0.75 g) in absolute ethanol (2.5 ml) at 0°–3° C. The reaction was stirred at 3° to 10° C. for 2 hours and then acidified to pH 3–4 with 2 N hydrochloric acid. The mixture was extracted with chloroform (3×10 ml). The aqueous phase was evaporated to dryness in vacuo and the residue was washed with ethyl acetate and ethanol. The organic washings were combined and evaporated in vacuo to give an oily solid (0.3 g). Purification by preparative layer chromatography on silica (20×20×0.2 cm) using a mixture of ethyl acetate:2-propanol:water:ammonia (25:15:8:1.5) as eluent gave a yellow oil (0.15 g). Conversion of the oil into its creatinine sulphate salt gave the title compound (0.14 g) as a colourless crystalline solid m.p. 190°–200° C.

Analysis Found: C, 46.35; H, 5.75; N, 16.15%; C$_{18}$H$_{19}$N$_3$O.1.66C$_4$H$_7$N$_3$O1.33H$_2$SO$_4$O.66C$_2$H$_6$O.2H$_2$O requires: C, 45.95; H, 6.1; H, 16.5%.

EXAMPLE 14

3-[2-(Methylamino)ethyl]-1H-indole-5-carboxamide compound with ethanol (10:1)

A solution of 3-[2-[(methyl(phenylmethyl)amino]ethyl]-1H-indole-5-carboxamide (1.05 g) in absolute ethanol (200 ml) was hydrogenated over pre-reduced palladium oxide on charcoal (10%, 0.5 g) for 2.5 hours at room temperature and pressure. The catalyst was filtered off and the filtrate evaporated in vacuo to give the title compound (0.7 g) as a colourless crystalline solid. T.L.C. Silica, ethanol:water (1:1) R$_f$0.3

Analysis Found: C, 66.3; H, 7.3; N, 18.7%; C$_{12}$H$_{15}$N$_3$O.0.1.C$_2$H$_6$O requires: C, 66.0; H, 7.1; N, 18.9%.

EXAMPLE 15

3-(2-Aminoethyl)-1H-indole-5-carbothioamide, compound with creatinine, sulphuric acid and water (4:5:4:10)

(i)

3-[2-(1,3-Dihydro-1,3-dioxo-2H-isoindol-2-yl)ethyl]-1H-indole-5-carbothioamide

Hydrogen sulphide gas was passed through a stirred solution of 3-[2-(1,3-dihydro-1,3-dioxo-2H-isoindol-2-yl)ethyl]-1H-indole-5-carbonitrile (4 g) and triethylamine (3 ml) in dry dimethylformamide (100 ml) for 6 hours. and the reaction mixture was stirred for a further 7 days. Hydrogen sulphide gas was passed through the reaction mixture for 0.5 hours on each day. Water (200 ml) was added and the mixture was extracted with ethyl acetate (3×200 ml). Evaporation of the washed (H$_2$O) and dried (MgSO$_4$) extracts gave a yellow residue which gave a yellow powder (4.1 g) on trituration with ether. A sample was crystallised from ethanol to give the title compound as yellow microcrystals m.p. 195°–8° C. (dec.)

Analysis Found: C, 65.05; H, 4.3; N, 11.65%; C$_{19}$H$_{15}$N$_3$O$_2$S requires: C, 65.3; H, 4.3; N, 12.0%.

(ii) 3-(2-Aminoethyl)-1H-indole-5-carbothioamide, compound with creatinine, sulphuric acid and water (4:5:4:10)

A solution of 3-[2-(1,3-dihydro-1,3-dioxo-2H-isoindol-2-yl)ethyl]-1H-indole-5-carbothioamide (2 g) in ethanolic methylamine (33%, 30 ml) was kept at 20° C. for 3.5h. and then was evaporated to dryness. The residue was chromatographed on silica (m.f.c. 60 g), eluted with ethyl acetate: 2-propanol:water:ammonia (25:15:4:0.5) to give the major component of the reaction mixture as a yellow gum (0.45 g). This was redissolved in hot aqueous ethanol (20%, 20.ml) and treated with aqueous creatinine and sulphuric acid solution (2 M, 1.0 ml) Pale yellow microcrystals (0.41 g) of the title compound m.p. 202°–5° C. (dec) separated out on cooling.

Analysis Found: C, 37.9; H, 5.3; N, 18.75%; C$_{11}$H$_{13}$N$_3$S.1.25C$_4$H$_7$N$_3$O.H$_2$SO$_4$.2.5H$_2$O requires: C, 38.15; H, 5.7; N, 18.85%.

EXAMPLE 16

3-(2-Aminoethyl)-1-(phenylmethyl)-1H-indole-5-carboxamide, compound with maleic acid and water (4:4:1)

(i) 3-[2-(1,3-Dihydro-1,3-dioxo-2H-isoindol-2-yl)ethyl]-1-(phenylmethyl)-1H-indole-5-carbonitrile Sodium hydride (0.16 g) was added to a solution of 3-[2-(1,3-dihydro-1,3-dioxo-2H-isoindol-2-yl)ethyl]-1H-indole-5-carbonitrile (2.0 g) in dry dimethylformamide (40 ml) under nitrogen. After 0.5 hour. benzyl chloride was added and after a further 2 hours the mixture was diluted with water (150 ml) and extracted with ethyl acetate (3×40 ml). Evaporation of the washed (H$_2$O) and dried (MgSO$_4$) extract gave a red oil which was triturated with ether and then crystallised from ethanol to give the title compound as yellow microcrystals (1.2 g) m.p. 182°–4° C. T.L.C. Silica, ether R$_f$0.45.

(ii) 3-(2-Aminoethyl)-1-(phenylmethyl)-1H-indole-5-carbonitrile, compound with maleic acid and water (4:4:1)

A mixture 3-[2-(1,3-dihydro-1,3-dioxo-2H-isoindol-2-yl)ethyl]-1-(phenylmethyl)-1H-indole-5-carbonitrile (1 g) and hydrazine hydrate (1 ml) in ethanol (40 ml) under nitrogen was heated at 60° C. for 2 hours. The solvent was evaporated off and the residue was treated with aqueous 2 N sodium carbonate solution (40 ml) at 50° C. for 0.5 hour. The mixture was extracted with ethyl acetate (3×40 ml) and the combined organic extracts were washed (H$_2$O) dried (MgSO$_4$) and concentrated to ca. 50 ml. A solution of maleic acid (0.3 g) in ethyl acetate (10 ml) was added to give the title compound as a yellow crystalline solid (0.7 g) m.p. 182°–4° C.

Analysis Found: C, 66.4; H, 5.4; N, 10.9% C$_{18}$H$_{17}$N$_3$.C$_4$H$_4$O$_4$.0.25H$_2$O requires: C, 66.75; H, 5.45; N, 10.6%.

(iii) 3-(2-Aminoethyl)-1-(phenylmethyl)-1H-indole-5-carboxamide, compound with maleic acid and water (4:4:1)

Following the method of Example 9(iii)a, treatment of 3-(2-aminoethyl)-1-(phenylmethyl)-1H-indole-5-carbonitrile (0.6 g) with Amberlite resin (5 g) gave the title compound as brown microcrystals (0.15 g) m.p. 188°–9° C.

Analysis Found: C, 63.15; H, 5.85; N, 10.4%; C$_{18}$H$_{19}$N$_3$O.C$_4$H$_4$O$_4$.0.25H$_2$O requires: C, 63.15; H, 5.85; N, 10.05%.

EXAMPLE 17

3-(2-Aminoethyl)-1-methyl-1H-indole-5-carboxamide, compound with maleic acid, methanol and water (4:4:4:1)

3-[2-(1,3-Dihydro-1,3-dioxo-2H-isoindol-2-yl)ethyl]-1-methyl-1H-indole-5-carbonitrile, compound with ethyl acetate (10:1)

Following the method Example 16(i), 3-[2-(1,3-dihydro-1,3-dioxo-2H-isoindol-2-yl)ethyl]-1H-indole-5-carbonitrile (3 g) and methyl iodide (1 ml) gave the title compound as pale yellow microcrystals (1.8 g) m.p. 212°–4° C.

Analysis Found: C, 71.8; H, 4.5; N, 12.5% C$_{20}$H$_{15}$N$_3$O$_2$.0.1C$_4$H$_8$O$_2$ requires: C, 72.1; H, 4.65; N, 12.35%.

(ii) 3-(2-Aminoethyl)-1-methyl-1H-indole-5-carbonitrile, compound with maleic acid and ethyl acetate (4:4:1)

Following the method of Example 16(ii), 3-[2-(1,3-dihydro-1,3-dioxo-2H-isoindol-2-yl)ethyl]-1-methyl-1H-indole-5-carbonitrile (1.0 g) and hydrazine hydrate (1 ml) gave the title compound as pale yellow needles (0.6 g) m.p. 163°–5° C.

Analysis Found: C, 60.7; H, 5.4; N, 12.5% C$_{12}$H$_{13}$N$_3$.C$_4$H$_4$O$_4$0.25C$_4$H$_8$O$_2$ requires: C, 60.5; H, 6.0; N, 12.6%.

(iii) 3-(2-Aminoethyl)-1-methyl-1H-indole-5-carboxamide, compound with maleic acid, methanol and water (4:4:4:1)

Following the method of Example 16(iii), treatment of 3-(2-aminoethyl)-1-methyl-1H-indole-5-carbonitrile, maleate (0.4 g) with Amberlite resin (5 g) gave the title compound as pale yellow needles (0.23 g) m.p. 161°–3° C.

Analysis Found: C, 54.5; H, 5.6; N, 11.45% C$_{12}$H$_{15}$N$_3$O.C$_4$H$_4$O$_4$.CH$_3$OH.0.25H$_2$O requires: C, 55.1; H, 6.0; N, 11.2%.

EXAMPLE 18

3-(3-Aminopropyl)-1H-indole-5-carboxamide, compound with water and ethyl acetate (10:5:1)

(i) 5-Bromo-3-(3-chloropropyl)-1H-indole

5-Chloropentanal (ca. 70% pure, 8.0 g) was added to a suspension of 4-bromophenylhydrazine hydrochloride (13.4 g) in aqueous acetic acid (50%, 300 ml). The mixture was heated rapidly to boiling with vigorous stirring and maintained at reflux for 7 hours. The resulting dark brown solution was cooled to room temperature, diluted with water (300 ml) and extracted with ethyl acetate (4×150 ml). The combined extracts were washed with water (200 ml) and saturated aqueous sodium hydrogen carbonate (4×250 ml), dried (MgSO$_4$), filtered and evaporated to a dark brown oil (14.7 g), which was purified on a silica column (Kieselgel 60, 200 g) eluted with ethyl acetate:light petroleum (b.p. 60°–80°) (1:2) followed by bulb to bulb distillation twice in vacuo to give the title compound as a yellow oil (4 g) b.p. 200° C., 0.5 mm, which rapidly darkened on storage.

Analysis Found: C, 48.2; H, 4.1; N, 5.2% C$_{11}$H$_{11}$BrClN requires: C, 48.5; H, 4.1; N, 5.1%.

(ii) 2-[3-[5-Bromo-1H-indol-3-yl]propyl]-1H-isoindole-1,3-(2H)-dione

A mixture of 5-bromo-3-(3-chloropropyl)-1H-indole (1.35 g), potassium phthalimide (0.93 g) and potassium iodide (1.3 g) in dry dimethylformamide (20 ml) was warmed with stirring at 105° C. for 3 hours. The mixture was cooled and diluted with water (30 ml). An oil precipitated which crystallised over the next 5 min. The resulting solid was collected and washed thoroughly with water. The product was recrystallised from 2-propanol (50 ml) to afford the title compound as a pale yellow crystalline solid (1.1 g) m.p. 168.5°–170° C.

Analysis Found: C, 59.9; H, 4.0; N, 7.2%; C$_{19}$H$_{15}$BrN$_2$O$_2$ requires: C, 59.5; H, 3.95; N, 7.3%.

(iii) 3-[3-(1,3-Dihydro-1,3-dioxo-2H-isoindol-2-yl)propyl]-1H-indole-5-carbonitrile 2-[3-[5-Bromo-1H-indol-3-yl]propyl]-1H-isoindole-1,3-(2H)-dione (8.43 g) and cuprous cyanide (3.2 g) were added to N-methyl-2-pyrrolidinone (20 ml) under a nitrogen atmosphere. The stirred mixture was heated to reflux over 25 min. and maintained at reflux for 45 min. It was then cooled to room temperature and poured onto ice-water (300 g). Concentrated aqueous ammonia (40 ml) and ethyl acetate (300 ml) were added and the mixture was stirred vigorously for 20 min. The brown organic layer was separated from the blue aqueous phase. The aqueous phase was then extracted with ethyl acetate (3×100 ml). The combined organic solutions were washed with water (3×100 ml) until the washings were colourless, dried (MgSO$_4$) and evaporated in vacuo to afford a fawn solid (6.85 g), which was recrystallised from a mixture of isopropyl acetate (300 ml) and 2-propanol (100 ml) to afford the title compound as a pale fawn solid (5.2 g) m.p. 193°–195° C.

Analysis Found: C, 73.3; H, 4.85; N, 12.3%; C$_{20}$H$_{15}$N$_3$O$_2$ requires: C, 73.0; H, 4.6; N, 12.8%.

(iv) 3-(3-Aminopropyl)-1H-indole-5-carbonitrile, hydrochloride.

Hydrazine hydrate (5.25 ml) was added to a suspension of 3-[3-(1,3-dihydro-1,3-dioxo-2H-isoindol-2-yl)propyl]-1H-indole-5-carbonitrile (4 g) in absolute ethanol (120 ml) at 60° C. The mixture was heated between 60°–80° C. for 2 hours. After 20 min. the solid had dissolved but a heavy cream precipitate formed after 40 min. The reaction mixture was cooled and evaporated in vacuo to a cream paste which was taken up into 2 N aqueous sodium carbonate (100 ml) and warmed at 40°–50° C. for 30 min. The solution and oil thus obtained was extracted with ethyl acetate (3×75 ml) and the combined extracts were washed with water (50 ml) dried (MgSO$_4$) and evaporated to afford an orange brown oil which crystallised on standing (2.27 g) m.p. 80°–85° C.

A portion of the product (0.7 g) was dissolved in ethyl acetate (25 ml) and treated with ethanolic hydrogen chloride. An off-white solid was precipitated which was collected, washed with ethyl acetate and recrystallised from a mixture of ethanol (20 ml) and ethyl acetate (35 ml) to afford the title compound as a finely-divided off-white solid. m.p. 232°–237° C.

Analysis Found: C, 60.9; H, 6.0; N, 17.7%; C$_{12}$H$_{13}$N$_3$.HCl requires: C, 61.1; H, 6.0; N, 17.8%.

(v) 3-(3-Aminopropyl)-1H-indole-5-carboxamide, compound with water and ethyl acetate (10:5:1)

A mixture of 3-(3-aminopropyl)-1H-indole-5-carbonitrile (1.45 g) and Amberlite resin (17 g) in water (100 ml) was heated at reflux for 4.5 hours. The resin was filtered off and the clear colourless filtrate evaporated in vacuo to afford a white solid (0.7 g) m.p. 189° C. Recrystallisation of the solid from a mixture of ethanol (15 ml), ethyl acetate (85 ml) and light petroleum (bp 60°–80° C.) (150 ml) gave the title compound as a very pale yellow solid (0.5 g) m.p. 188°–194° C.

Analysis Found: C, 63.5; H, 6.8; N, 17.9% C$_{12}$H$_{15}$N$_3$O.0.5H$_2$O.0.1C$_4$H$_8$O$_2$ requires: C, 63.1; H, 7.2; N, 17.9%

EXAMPLE 19

3-(2-Aminopropyl)-1H-indole-5-carboxamide, compound with maleic acid and water (2:2:1)

(i) 3-(Dimethylaminomethyl)-1H-indole-5-carboxamide, compound with creatinine, sulphuric acid and water (2:2:2:3)

A mixture of aqueous formaldehyde (36%, 0.56 g) and aqueous dimethylamine (40%, 0.76) was added to solution of 1H-indole-5-carboxamide (1 g) in glacial acetic acid (50 ml) and the reaction mixture was stirred at 25° C. for 2 hours. The solvent was evaporated at reduced pressure and the residue was treated with aqueous 2 N sodium hydroxide (15 ml) at 10° C. The mixture was extracted with ethyl acetate (3×30 ml) and evaporation of the washed (H$_2$O) and dried (MgSO$_4$) extracts gave a white foam (0.7 g). This was redissolved in hot aqueous ethanol (80%, 50 ml) and the solution was treated with a solution of creatinine sulphate (0.8 g) in water (10 ml). Dilution with ethanol (100 ml) and cooling gave the title compound as white needles (0.8 g). m.p. 165°–8° C.

Analysis Found: C,42.1;H,6.2;N,18.8%, C$_{12}$H$_{15}$N$_3$O.C$_4$H$_7$N$_3$O.H$_2$SO$_4$.1.5H$_2$O requires:C,42.2;H,5.9;N,18.5%.

(ii) 3[(2-Methyl-2-nitro)ethyl]-1H-indole-5-carboxamide

Sodium (0.1 g) was added to dry nitroethane (50 ml) and the mixture was stirred under nitrogen until all the sodium had dissolved (0.5 hour). A solution of 3-(dimethylaminomethyl)-1H-indole-5-carboxamide (2.5 g) in nitroethane (50 ml) was added and the reaction mixture was heated under reflux for 5 hours. The nitroethane was removed by distillation at reduced pressure, and the residue was redissolved in ethyl acetate (100 ml). Evaporation of the washed (2N HCl, H$_2$O) and dried (MgSO$_4$) ethyl acetate solution gave the title compound as a pale yellow solid which crystallised from toluene-ethanol as cream microcrystals (2.21 g) m.p. 164°–5° C.

Analysis Found: C, 58.6; H, 5.7; N, 16.6%, C$_{12}$H$_{13}$N$_3$O$_3$ requires: C, 58.3; H,5.3; N,17.0%.

(iii) 3-(2-Aminopropyl)-1H-indole-5-carboxamide, compound with maleic acid and water (2:2:1)

A mixture of 3[(2-methyl-2-nitro)ethyl]-1H-indole-5-carboxamide (1 g), Raney nickel (1 g) and ethanol (100 ml) was stirred in a hydrogen atmosphere for 3 hours. The reaction mixture was filtered and the filtrate was concentrated to about 25 ml. A solution of maleic acid (0.5 g) in ethanol (25 ml) was added and after 0.2 hours the solution was diluted with ether (150 ml). Repeated trituration of the resulting gum with dry ether gave a light brown solid which was filtered off and dried to give the title compound (0.68 g) m.p. 180°–4° C.

Analysis Found: C, 56.3; H, 5.95; N, 11.9%, C$_{12}$H$_{15}$N$_3$O.C$_4$H$_4$O$_4$.½H$_2$O requires: C, 56.15; H, 5.85; N, 12.25%.

EXAMPLE 20

3-(2-Aminoethyl)-2-methyl-1H-indole-5-carboxamide, compound with hydrochloric acid and methanol (10:20:1)

(i) 3-(2-Aminoethyl)-2-methyl-1H-indole-5-carbonitrile, maleate

4-Cyanophenylhydrazine hydrochloride (3 g) was shaken with sodium hydroxide (2N, 70 ml) and ethyl acetate (100 ml). The dried (Na$_2$SO$_4$) organic extract was evaporated in vacuo to give an orange solid (2.2 g). 5-Chloropentan-2-one (2 g), methanol (50 ml) and water (4 ml) were added to the solid and the mixture was heated under reflux for 42 hours. The solvent was distilled off and the residue was dissolved in potassium carbonate (20%, 50 ml) and the solution was extracted with ethyl acetate (2×150 ml, 70 ml). The dried (Na$_2$SO$_4$) extracts were evaporated in vacuo to give a brown oil (4.1 g) which was converted into the maleate salt to give the title compound (2.65 g) as an off-white crystalline solid m.p. 177.5°–179° C.

Analysis Found: C, 60.9; H, 5.6; N, 13.4%. C$_{12}$H$_{13}$N$_3$.C$_4$H$_4$O$_4$ requires: C, 60.9; H,5.4; N, 13.3%.

(ii) 3-(2-Aminoethyl)-2-methyl-1H-indole-5-carboxamide, compound with hydrochloric acid and methanol (10:20:1)

3-(2-Aminoethyl)-2-methyl-1H-indole-5-carbonitrile, maleate (1.2 g) was hydrolysed with Amberlite resin (32 g) as described in Example 9(iii)a and gave after conversion into the hydrochloride salt the title compound (0.84 g) as a buff crystalline solid m.p. 208°–212° C.

Analysis Found: C, 49.7; H, 5.9; N, 41.1; C$_{12}$H$_{15}$N$_3$O.2HCl.0.1MeOH requires: C, 49.6; H, 6.0; N, 14.3;

Analysis Found: Cl, 24.0%; C$_{12}$H$_{15}$N$_3$O.2HCl.O.1-MeOH requires: Cl, 24.2%.

EXAMPLE 21

3-(2-Aminoethyl)-2-methyl-1H-indole-5-carboxamide, compound with hydrochloric acid and methanol (10:20:1)

A solution of 4-hydrazinobenzamide (0.5 g) and 5-chloropentan-2-one (0.55 g) in methanol (10 ml) and water (1 ml) was refluxed for 13 hours. The solvent was evaporated in vacuo and the residue dissolved in methanol (10 ml) and the insoluble material removed by filtration through Hyflo. Excess ethereal hydrogen chloride was added to the filtrate and the product precipitated by the addition of ethyl acetate (25 ml) and ether (150 ml). Crystallisation from a mixture of methanol and ethyl acetate gave the title compound as buff crystals (0.3 g) m.p. 207°–213° C. T.L.C. Silica, methanol: ammonia (20:1) R$_f$ 0.4.

EXAMPLE 22

3-(2-Aminoethyl)-2-phenyl-1H-indole-5-carboxamide, maleate (i) 3-(2-Aminoethyl)-2-phenyl-1H-indole-5-carbonitrile, maleate Following the method described in Example 20, 4-cyanophenylhydrazine 3.3 g) and γ-chlorobutyrophenone (4.8 g) gave the title compound (3.23 g) as a cream crystalline solid m.p. 200°–202° C.

Analysis Found: C, 67.2; H, 5.0; N, 10.9%. $C_{17}H_{15}N_3C_4H_4O_4$ requires: C, 66.8; H, 5.1; N, 11.1%.

(ii) 3-(2-Aminoethyl)-2-phenyl-1H-indole-5-carboxamide, maleate 3-(2-Aminoethyl)-2-phenyl-1H-indole-5-carbonitrile, maleate (2 g) was hydrolysed with Amberlite resin (50 g) as described in Example 9(iii)a and gave after conversion into the maleate salt the title compound (0.68 g) as a colourless crystalline solid m.p. 188.5°–190.5° C.

Analysis Found: C, 63.6; H, 5.5; N, 10.4%; $C_{17}H_{17}N_3O.C_4H_4O$ requires: C, 63.8; H, 5.4; N, 10.6%.

EXAMPLE 23

3-(2-Aminoethyl)-1H-indole-5-carboxamide 3-(2-Aminoethyl-1H-indole-5-carbonitrile (10.0 g) was stirred with Amberlite resin (90 g) in water (155 ml) at reflux for 17 hours. The resin was filtered off and washed with hot water and hot ethanol. The ethanolic and aqueous washings were combined and evaporated in vacuo to give a pale yellow solid (5.0 g). Crystallisation from water gave the title compound (3.0 g) as an off-white solid m.p. 173°–6° C. T.L.C. silica, ethyl acetate, 2-propanol, water, ammonia (25:15:8:2) R$_f$ 0.33.

EXAMPLE 24

3-(2-Aminoethyl)-1H-indole-5-carboxamide, maleate

A mixture of 3-(2-aminoethyl)-1H-indole-5-carbonitrile (2 g) and finely ground potassium hydroxide (10 g) in 2-methyl-2-propanol (50 ml) and dimethyl sulphoxide (2 ml) was stirred and heated under reflux for 3 days. The mixture was cooled and diluted with water (50 ml) and extracted with ethyl acetate (2×50 ml). The combined extracts were evaporated to give a yellow oil (2.9 g). Conversion of the oil into its maleate salt in 2-propanol followed by crystallisation from aqueous ethanol gave the title compound (1.9 g) as a buff crystalline solid m.p. 166°–8° C. T.L.C. Silica, ethyl acetate, 2-propanol, water, ammonia (25:15:8:2) R$_f$ 0.33.

EXAMPLE 25

3-(2-Aminoethyl)-1H-indole-5-carboxamide (i)
4[[4-(1,3-Dihydro-1,3-dioxo-2H-isoindol-2-yl)butylidene]hydrazino]benzamide A solution of 4-hydrazinobenzamide (0.26 g), in 25% aqueous acetic acid (20 ml) was added to 4-[1,3-dihydro-1,3-dioxo-2H-isoindol-2-yl]-butanal diethyl acetal (0.5 g). The mixture was heated on a steam bath for 2 hours and then cooled. The mixture was decanted to leave an oil which was triturated with methanol (3 ml). The solid that resulted was washed with water (5 ml) and dried in vacuo at 50° C. to give the title compound (0.55 g) as a yellow crystalline solid m.p. 147°–152° C. (decomp).

TLC (Silica/ethyl acetate) Rf 0.4

(ii)
2-[2-[1,3-Dihydro-1,3-dioxo-2H-isoindol-2-yl]ethyl]-1H-indole-5-carboxamide An intimate mixture of the benzamide prepared as in (i) above (4.5 g), and powdered, fused zinc chloride (2 g) was heated between 140° and 165° C. for 30 min. The resulting glass-like solid was dissolved in boiling acetic acid (200 ml) and the cooled solution was decanted from some residual gum. Hydrogen sulphide gas was bubbled through the solution and the precipitated zinc salts were filtered off. The filtrate was basified with 0.88 ammonia to pH 8–9 to precipitate the product as a yellow solid (2.7 g) which was recrystallised from a mixture of toluene and methanol to give the title carboxamide m.p. 255°–260° C.(decomp).

T.L.C. (Silica/ethyl acetate:petroleum spirit b.p. 60°–80° C.) (9:1) Rf 0.4

(iii) 3-[2-Aminoethyl]-1H-indole-5-carboxamide compound with creatinine, sulphuric acid and water Hydrazine hydrate (30 ml) was added to the crude phthalimido carboxamide prepared in (ii) above (1.5 g) in ethanol (60 ml). The mixture was refluxed for 2.5 hours and cooled. The solvent was evaporated off and the residue stirred with 2 N sodium carbonate solution (60 ml) and the resulting solution was evaporated to dryness. The residue was extracted with ethanol and the combined extracts were evaporated to give a yellow solid that was dissolved in hot ethanol (45 ml) and treated with a solution of creatinine sulphate (1.6 g) in water (20 ml) and ethanol (10 ml). The solution obtained was diluted with ethanol to 85 ml. The title compound (1.8 g) precipitated as an off-white solid m.p. 205°–210° C.

EXAMPLE 26

3-(2-Aminoethyl)-1H-indole-5-carboxamide

[2-[5-(Aminocarbonyl)-1H-indol-3-yl]ethyl]carbamic acid, phenylmethyl ester (0.15 g) in ethanol (20 ml) was hydrogenated over palladium oxide on charcoal (10%, 0.2 g; prehydrogenated). Absorption of hydrogen (7 ml) was complete within three minutes.

The catalyst was filtered off and the solvent was evaporated in vacuo to give a colourless oil (0.08 g).

A solution of this oil in ethanol (5 ml) and water (1 ml) was heated under reflux and a solution of creatinine sulphate (0.11 g) in water (1 ml) was added. The crystalline solid that precipitated on cooling was filtered off to give the title compound as its hydrated creatinine sulphate salt (0.115 g) as a colourless crystalline solid m.p. 205°–210° C.

T.L.C. (Silica/ethyl acetate:propan-2-ol:water:ammonia, 25:15:8:2) Rf 0.35

EXAMPLE 27

3-(2-Aminoethyl)-1H-indole-5-carboxamide, maleate, compound with ethanol (2:2:1)

A mixture of 3-[2-(1,3-dihydro-1,3-dioxo-2H-isoindol-2-yl)ethyl]-1H-indole-5-carboxamide (0.3 g), ethanol (2 ml) and ethanolic methylamine (33%, 1 ml) was stirred at room temperature for 1.5 hours, and the mixture becoming homogenous after 5 min. The solvent was evaporated in vacuo to leave a yellow oil. The oil was dissolved in ethanol (2 ml) and a solution of maleic acid (0.1 g) in ethanol (1 ml) was added,. The solid which precipitated was filtered off and dried to give the title compound (0.12 g) as a white crystalline solid. T.L.C. Silica, ethyl acetate:2-propanol:water:ammonia (25:15:8:2) $R_f$ 0.33.

EXAMPLE 28

Recrystallisation of 3-(2-aminoethyl)-1H-indole-5-carboxamide, maleate 3-(2-Aminoethyl)-1H-indole-5-carboxamide maleate, compound with ethanol (2:2:1) (10 g) was dissolved in hot water (50 ml) to give a clear yellow solution, which was cooled to room temperature with stirring. The resulting solid was filtered off and dried at 50° C. in vacuo to give the title compound (8.6 g) as a white crystalline solid m.p. 180°-183° C. T.L.C. Silica, ethyl acetate:2-propanol:water:ammonia (25:15:8:2) $R_f$ 0.4

Analysis Found: C, 56.47; H, 5.33; N, 13.19%; $C_{11}H_{13}N_3O.C_4H_4O_4$ requires: C, 56.4; H, 5.37; N, 13.16%.

EXAMPLE 29

3-(2-Aminoethyl)-1H-indole-5-carboxamide, maleate

A solution of 3-(2-Aminoethyl)-1H-indole-5-carbonitrile (2 g) and potassium t-butoxide (12 g) in a mixture of t-butanol (50 ml) and dimethyl sulphoxide (3 ml) was stirred under reflux for 72 hours. The mixture was cooled and diluted with water (50 ml). The product was extracted into ethyl acetate (2×50 ml) and the dried ($Na_2SO_4$) extracts were evaporated to leave a yellow oil (3 g). The oil was dissolved in 2-propanol (10 ml) and the resulting solution was added to a hot solution of maleic acid (1.25 g) in 2-propanol (20 ml). The solution was cooled to room temperature and diluted with ethyl acetate (50 ml). The precipitated solid was filtered off and dried at 50° C. to give the title compound (1.6 g) as a white solid m.p. 161°-2° C. T.L.C. Silica, ethyl acetate:2-propanol:water:ammonia (25:15:8:2) $R_f$ 0.4.

EXAMPLE 30

3-(2-Aminoethyl)-1-butyl- 1H-indole-5-carboxamide, compound with creatinine, sulphuric acid and water (8:10:9:16)

(i) [2-[5-(Aminocarbonyl)-1-butyl-1H-indol-3-yl]ethyl]carbamic acid, phenylmethyl ester Following the method of Example 16(i), [2-[5-(aminocarbonyl)-1H-indol-3-yl]ethyl]carbamic acid, phenylmethyl ester (1.5 g), sodium hydride (0.16 g) and 1-bromobutane (1 ml) gave a pale brown oily solid (1.5 g). Chromatography on a silica column (Kieselgel 60, 60 g) eluted with chloroform containing 1% methanol gave the title compound (1.0 g) as a colourless crystalline solid m.p. 138°-9° (ethyl acetate).

Analysis Found: C, 70.0; H, 6.9; N, 10.4%; $C_{23}H_{27}N_3O_3$ requires: C, 70.2; H, 6.9; N, 10.7%.

(ii) 3-(2-Aminoethyl)-1-butyl-1H-indole-5-carboxamide, compound with creatinine, sulphuric acid and water (8:10:9:16)

A solution of [2-[5-(aminocarbonyl)-1-butyl-1H-indol-3-yl]ethyl]carbamic acid, phenylmethyl ester (1 g) in Analar ethyl acetate (60 ml) was hydrogenated at room temperature and pressure over palladium oxide on charcoal (10%, 0.5 g; pre-reduced) until hydrogen uptake ceased. The mixture was filtered through a Hyflo pad and the filtrate evaporated to dryness to give a colourless solid (0.28 g). This material was purified on a silica column (Kieselgel 60, 25 g) eluted with a mixture of ethyl acetate:2-propanol:water:ammonia (25:15:4:1) to give a colourless oil (0.15 g) which was converted into its creatinine sulphate salt to give the title compound (0.17 g) as a colourless solid m.p. 143°-148° C.

Analysis Found: C, 43.95; H, 6.4; N, 17.2%; $8C_{15}H_{21}N_3O.10C_4H_7N_3O.9H_2SO_4.16H_2O$ requires: C, 43.9; H, 6.7; N, 17.3%.

I claim:
1. An indole of the general formula (I):

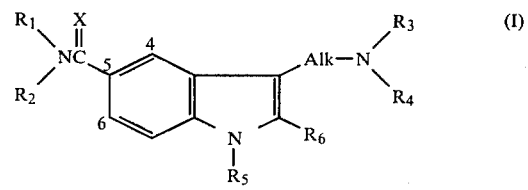

wherein $R_1$ and $R_2$, which may be the same or different, each represents a hydrogen atom, or an aryl, aralkyl, cycloalkyl, fluoroalkyl or alkyl group, which alkyl group may be unsubstituted or substituted by an alkenyl group or by a group —$OR_7$ or by a group

where $R_7$ and $R_8$, which may be the same or different, each represents a hydrogen atom, an alkyl, aryl or aralkyl group; or $R_1$ and $R_2$ together with the nitrogen atom to which they are attached form a saturated monocyclic 5 to 7 membered ring which may contain a further hetero function (viz oxygen or the group

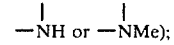

$R_3$ and $R_4$, which may be the same or different, each represents a hydrogen atom, or an aryl, aralkyl, cycloalkyl, fluoroalkyl or alkyl group, which alkyl group may be unsubstituted or substituted by an alkenyl group or by a group —$OR_7$ or by a group

where $R_7$ and $R_8$ are as previously defined;
or $R_3$ and $R_4$ may together form an aralkylidene group;
or $R_3$ and $R_4$ together with the nitrogen atom to which they are attached form a saturated monocyclic 5 to 7 membered ring which may contain a further hetero function (viz oxygen or the group $$-\overset{|}{N}H \text{ of } -\overset{|}{N}Me);$$

$R_5$ represents a hydrogen atom or an alkyl or aralkyl group;

$R_6$ represents a hydrogen atom or an aryl or $C_1$–$C_3$ alkyl group;

Alk represents an alkylene group of one to four carbon atoms in chain length, which group may be unsubstituted or substituted at one or more of its carbon atoms by one to three $C_1$–$C_3$ alkyl groups; and X represents an oxygen or sulphur atom,
and physiologically acceptable salts or hydrates.

2. An indole according to claim 1, wherein $R_1$ and $R_2$ both represent hydrogen atoms.

3. An indole according to claim 1 or 2, wherein one or both of $R_3$ and $R_4$ represent hydrogen atoms or $C_1$–$C_3$ alkyl groups or $R_3$ represents a hydrogen atom and $R_4$ is an aralkyl group.

4. An indole according to claim 1, wherein $R_5$ and $R_6$ both represent hydrogen atoms.

5. An indole according to claim 1, wherein Alk represents a $C_2$–$C_3$ alkylene group.

6. An indole according to claim 1, wherein X represents an oxygen atom.

7. An indole according to claim 1, wherein
$R_1$ represents a hydrogen atom;
$R_2$ represents a hydrogen atom or an aralkyl, cycloalkyl or alkyl group which alkyl group may be unsubstituted or substituted by an alkenyl group or by the group —$OR_7$;
$R_3$ represents a hydrogen atom or an alkyl group;
$R_4$ represents a hydrogen atom or an aralkyl, fluoroalkyl or an unsubstituted alkyl group or $R_3$ and $R_4$ together form an aralkylidene group or together with the nitrogen atom to which they are attached form a saturated monocyclic 5 to 7 membered ring containing a further hetero function;
$R_5$ represents a hydrogen atom, an alkyl group or a benzyl group;
$R_6$ represents a hydrogen atom or an alkyl group; and
Alk represents an alkylene group containing 2 or 3 carbon atoms.

8. An indole according to claim 1, wherein
$R_1$ represents a hydrogen atom;
$R_2$ represents a hydrogen atom or a methyl or hydroxymethyl group;
$R_3$ represents a hydrogen atom or a methyl group;
$R_4$ represents a hydrogen atom or a methyl, trifluoroethyl or benzyl group or the group $CH_3CH(CH_2)_2Ph$ (where Ph is an unsubstituted phenyl group); or
$R_3$ and $R_4$ together with the nitrogen atom to which they are attached represents a benzylidene or morpholino group;
$R_5$ represents a hydrogen atom or a methyl group;
$R_6$ represents a hydrogen atom;
Alk represents an unsubstituted alkylene group containing 2 or 3 carbon atoms; and
X is an oxygen atom.

9. An indole of general formula (I):

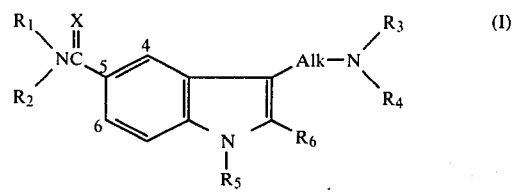

wherein
$R_1$ and $R_2$, which may be the same or different, each represents a hydrogen atom, or an aryl, aralkyl, cycloalkyl or alkyl group, which alkyl group may be unsubstituted or substituted by an alkenyl group or by a group —$OR_7$ or by a group $$-N\begin{matrix}R_7\\R_8\end{matrix}$$

where $R_7$ and $R_8$, which may be the same or different, each represents a hydrogen atom, an alkyl, aryl or aralkyl group; or $R_1$ and $R_2$ together with the nitrogen atom to which they are attached form a saturated monocyclic 5 to 7 membered ring which may contain a further hetero function (viz oxygen or the group $$-\overset{|}{N}H \text{ or } -\overset{|}{N}Me);$$

$R_3$ and $R_4$, which may be the same or different, each has the same meanings as defined for $R_1$ and $R_2$ but $R_3$ and $R_4$ are not necessarily the same as $R_1$ and $R_2$;

$R_5$ and $R_6$ which may be the same or different, each represents a hydrogen atom or a $C_1$–$C_3$ alkyl group;

Alk represents an alkylene group of one to four carbon atoms in chain length, which group may be unsubstituted or substituted at one or more of its carbon atoms by one to three $C_1$–$C_3$ alkyl groups; and X represents an oxygen or sulphur atom,
and its physiologically acceptable salts or hydrates.

10. 3-(2-Aminoethyl)-1H-indole-5-carboxamide and its physiologically acceptable salts.

11. A compound selected from
3-[2-[1-methyl-3-phenylpropyl)amino]ethyl]-1H-indole-5-carboxamide;
3-[2-(dimethylamino)ethyl]-1H-indole-5-carboxamide;
3-[2-(methylamino)ethyl]-1H-indole-5-carboxamide;
3-[2-(4-morpholinyl)ethyl]-1H-indole-5-carboxamide;
3-(2-aminoethyl)-1H-indole-5-carbothioamide;
3-(3-aminopropyl)-1H-indole-5-carboxamide;
3-[2-(2,2,2-trifluoroethyl)aminoethyl]-1H-indole-5-carboxamide and their physiologically acceptable salts.

12. 3-(2-Aminoethyl)-H-indole-5-carboxamide maleate.

13. A pharmaceutical composition for treating hypertension, Raynaud's Disease or migrane comprising a compound according to claims 1, 2, 4, 5, 6, 7, 8, 9, 10, 11, or 12 together with one or more physiologically acceptable carriers or excipients.

14. A method for the treatment of a patient suffering from hypertension, Raynaud's Disease or migrane which comprises administreing to the patient an effective amount of the composition according to claim 13.

* * * * *